United States Patent
Lipkens et al.

(10) Patent No.: US 10,640,760 B2
(45) Date of Patent: May 5, 2020

(54) THERAPEUTIC CELL WASHING, CONCENTRATION, AND SEPARATION UTILIZING ACOUSTOPHORESIS

(71) Applicant: FloDesign Sonics, Inc., Wilbraham, MA (US)

(72) Inventors: Bart Lipkens, Hampden, MA (US); Walter M. Presz, Jr., Wilbraham, MA (US); Brian Dutra, East Longmeadow, MA (US); Rudolf Gilmanshin, Framingham, MA (US); Jason Dionne, Simsbury, CT (US); Chris Leidel, Cambridge, MA (US); Louis Masi, DelMar, CA (US); Goutam Ghoshal, Springfield, MA (US); Kedar Chitale, Vernon, CT (US)

(73) Assignee: FloDesign Sonics, Inc., Wilbraham, MA (US)

( * ) Notice: Subject to any disclaimer, the term of this patent is extended or adjusted under 35 U.S.C. 154(b) by 142 days.

(21) Appl. No.: 15/586,116

(22) Filed: May 3, 2017

(65) Prior Publication Data

US 2017/0321208 A1 Nov. 9, 2017

Related U.S. Application Data

(60) Provisional application No. 62/374,910, filed on Aug. 15, 2016, provisional application No. 62/359,182, (Continued)

(51) Int. Cl.
*B06B 1/00* (2006.01)
*B08B 7/00* (2006.01)
(Continued)

(52) U.S. Cl.
CPC ............ *C12N 13/00* (2013.01); *A61J 3/00* (2013.01); *C12M 23/14* (2013.01); *C12M 25/14* (2013.01);
(Continued)

(58) Field of Classification Search
CPC ...... B01D 43/00; B01D 21/283; C12N 13/00; B06B 1/0622; B01J 19/10; C02F 1/36
(Continued)

(56) References Cited

U.S. PATENT DOCUMENTS 2,473,971 A 6/1949 Ross
2,667,944 A 2/1954 Crites
(Continued)

FOREIGN PATENT DOCUMENTS

CN 105 087 788 A 11/2015
DE 30 27 433 A1 2/1982
(Continued)

OTHER PUBLICATIONS

Alvarez et al.; Shock Waves, vol. 17, No. 6, pp. 441-447, 2008.
(Continued)

*Primary Examiner* — Monzer R Chorbaji
(74) *Attorney, Agent, or Firm* — FloDesign Sonics, Inc.

(57) ABSTRACT

Multi-stage acoustophoretic devices for continuously separating a second fluid or a particulate from a host fluid are disclosed. Methods of operating the multi-stage acoustophoretic devices are also disclosed. The systems may include multiple acoustophoretic devices fluidly connected to one another in series, each acoustophoretic device comprising a flow chamber, an ultrasonic transducer capable of creating a multi-dimensional acoustic standing wave, and a reflector. The systems can further include pumps and flowmeters.

27 Claims, 32 Drawing Sheets
(29 of 32 Drawing Sheet(s) Filed in Color)

Related U.S. Application Data filed on Jul. 6, 2016, provisional application No. 62/330,947, filed on May 3, 2016.

(51) Int. Cl.

| | | |
|---|---|---|
| *C12N 13/00* | (2006.01) | |
| *A61J 3/00* | (2006.01) | |
| *C12M 1/00* | (2006.01) | |
| *C12N 1/02* | (2006.01) | |
| *C12M 1/12* | (2006.01) | |

(52) U.S. Cl.
CPC ............ *C12M 47/02* (2013.01); *C12M 47/04* (2013.01); *C12N 1/02* (2013.01)

(58) Field of Classification Search
USPC .............................. 422/127–128, 292; 134/1
See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |

(56) References Cited

U.S. PATENT DOCUMENTS

| | | |
|---|---|---|
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Marieila, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn, Jr. et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugharn, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0321129 A1 | 11/2015 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |

FOREIGN PATENT DOCUMENTS

| | | | |
|---|---|---|---|
| DE | 32 18 488 A1 | 11/1983 | |
| DE | 196 48 519 A1 | 6/1998 | |
| DE | 103 19 467 B3 | 7/2004 | |
| DE | 10 2008 006 501 A1 | 9/2008 | |
| EP | 0 292 470 B1 | 11/1988 | |
| EP | 0 641 606 | 3/1995 | |
| EP | 1 175 931 A1 | 1/2002 | |
| EP | 1 254 669 B1 | 11/2002 | |
| GB | 2 420 510 A | 5/2006 | |
| JP | 9-136090 | 5/1997 | |
| RU | 2085933 | 7/1997 | |
| SU | 629496 | 10/1978 | |
| WO | WO 1987/07178 A1 | 12/1987 | |
| WO | WO 89/11899 A1 | 12/1989 | |
| WO | WO 90/05008 | 3/1990 | |
| WO | WO 97/34643 | 9/1997 | |
| WO | WO 1998/017373 | 4/1998 | |
| WO | WO 98/50133 A1 | 11/1998 | |
| WO | WO 02/072234 A1 | 9/2002 | |
| WO | WO 03/089567 | 10/2003 | |
| WO | WO 2004/079716 A1 | 9/2004 | |
| WO | WO 2009/063198 | 5/2009 | |
| WO | WO-2009063198 A2 * | 5/2009 | ......... C12N 15/1003 |
| WO | WO 2009/111276 A1 | 9/2009 | |
| WO | WO 2009/144709 A1 | 12/2009 | |
| WO | WO 2010/024753 A1 | 4/2010 | |
| WO | WO 2010/040394 A1 | 4/2010 | |
| WO | WO 2011/023949 A2 | 3/2011 | |
| WO | WO 2011/025890 A1 | 3/2011 | |

(56) References Cited

FOREIGN PATENT DOCUMENTS

| WO | WO 2011/027146 A2 | 3/2011 | |
|---|---|---|---|
| WO | WO 2011/131947 A2 | 10/2011 | |
| WO | WO 2011/161463 A2 | 12/2011 | |
| WO | WO 2013/043297 A1 | 3/2013 | |
| WO | WO 2013/049623 A1 * | 4/2013 | ............... A61J 3/00 |
| WO | WO 2013/055517 A1 | 4/2013 | |
| WO | WO 2013/138797 A1 | 9/2013 | |
| WO | WO 2013/148376 | 10/2013 | |
| WO | WO 2013/159014 A1 | 10/2013 | |
| WO | WO 2014/014941 A1 | 1/2014 | |
| WO | WO 2014/029505 | 2/2014 | |
| WO | WO 2014/055219 A2 | 4/2014 | |
| WO | WO 2014/124306 A1 | 8/2014 | |
| WO | WO 2014/153651 | 10/2014 | |
| WO | WO 2015/006730 | 1/2015 | |
| WO | WO 2016/176663 A1 | 11/2016 | |
| WO | WO 2017/041102 A1 | 3/2017 | |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; Frequency sweeping and fluid flow effects on particle trajectories ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Separation of bacterial spores from flowering water in macro-scale cavities by ultrasonic standing waves; submitted/ uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report, dated Jul. 18, 2013.
European Search Report of European Application No. 11769474.5, dated Sep. 5, 2013.
European Search Report of European Application No. 13760840.2, dated Feb. 4, 2016.
European Search Report of European Application No. 13721179.3 dated Feb. 23, 2016.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 dated Jun. 21, 2013.
International Search Report and Written Opinion of International Application No. PCT/US2013/032705 dated Jul. 26, 2013.
International Search Report and Written Opinion of International Application No. PCT/US2013/050729 dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.

(56) References Cited

OTHER PUBLICATIONS

International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
Augustsson et al., Acoustophoretic microfluidic chip for sequential elution of surface bound molecules from beads or cells, Biomicrofluidics, Sep. 2012, 6(3):34115.
International Search Report and Written Opinion for International Application No. PCT/US2017/030903 dated Jul. 19, 2017.

\* cited by examiner

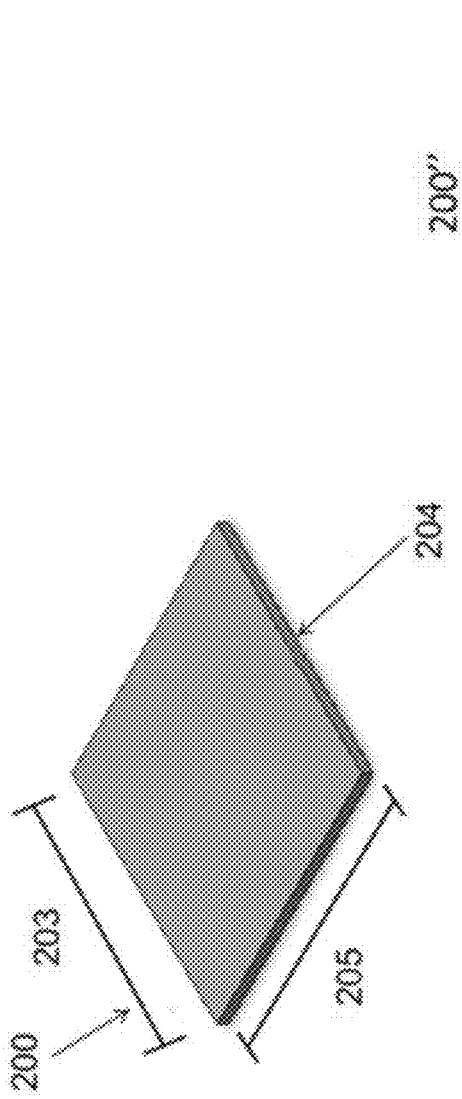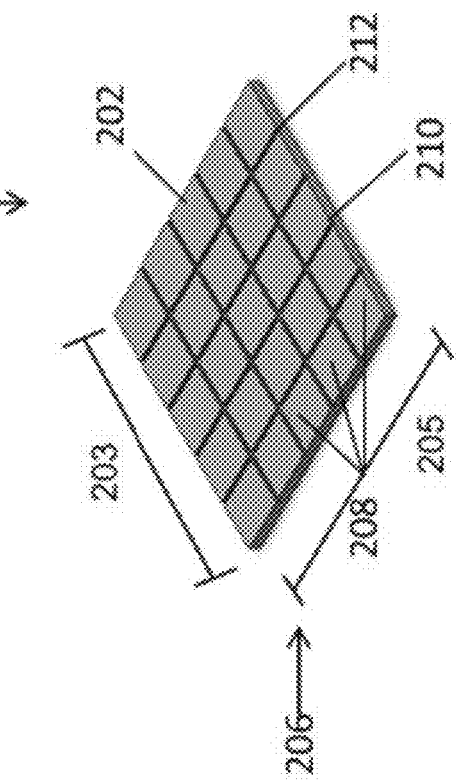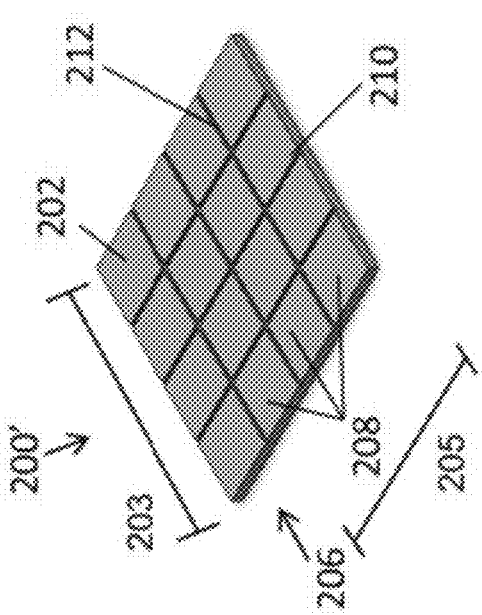

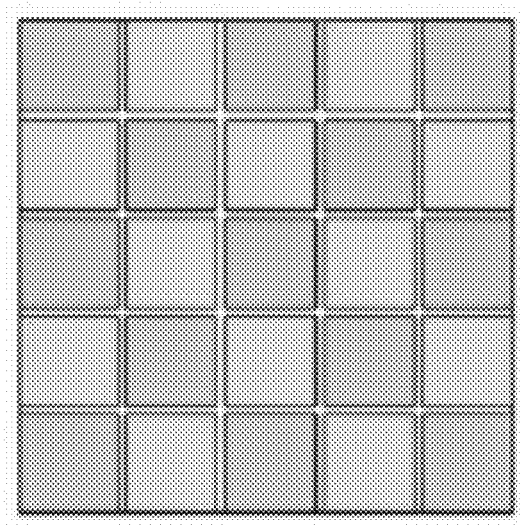
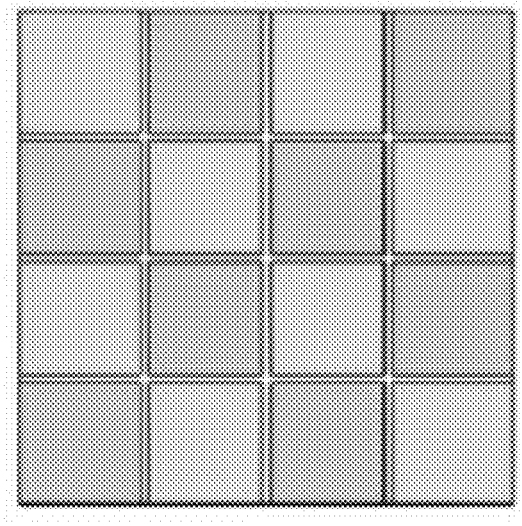
FIG. 11
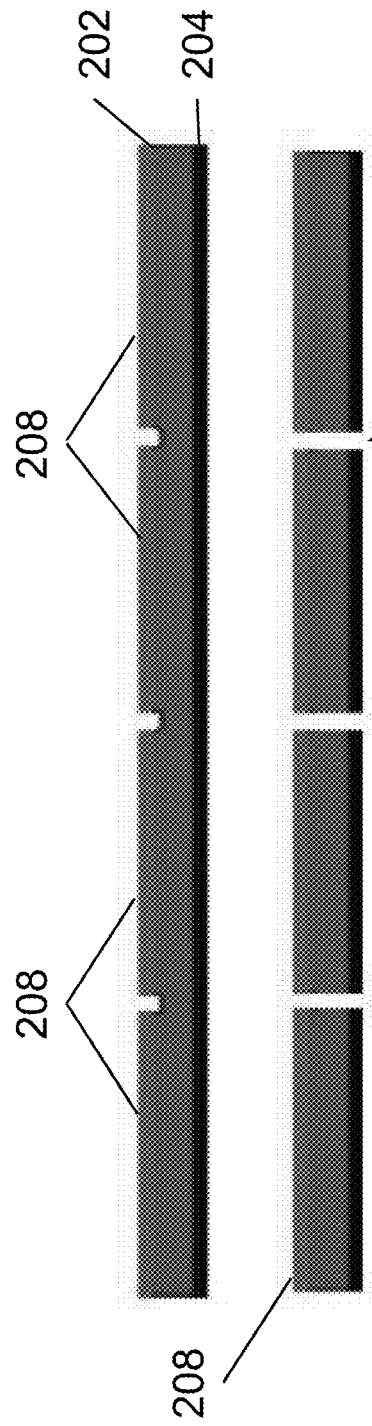
FIG. 12

US 10,640,760 B2

THERAPEUTIC CELL WASHING, CONCENTRATION, AND SEPARATION UTILIZING ACOUSTOPHORESIS

CROSS-REFERENCE TO RELATED APPLICATIONS

This application claims priority to U.S. Provisional Patent Application Ser. No. 62/330,947, filed on May 3, 2016, and to U.S. Provisional Patent Application Ser. No. 62/359,182, filed on Jul. 6, 2016, and to U.S. Provisional Patent Application Ser. No. 62/374,910, filed on Aug. 15, 2016. The disclosures of these applications are hereby fully incorporated herein by reference in their entirety.

BACKGROUND

Concentrating therapeutic cells and transferring them from one solution into another (usually referred to as washing) are two processes involved at multiple stages of production and use of the cells. The washing and separation of materials in cellular processing is an important part of the overall efficacy of the cell therapy of choice. In particular, therapeutic cells may originally be suspended in a growth serum or in preservative materials like dimethyl sulfoxide (DMSO). Separating the cells from these fluids so the cells can be further processed is important in the overall therapeutic process of using such cellular materials. In one example, the cells are typically recovered from a bioreactor, concentrated, and transferred from culture media into an electroporation buffer prior to transduction, such as in manufacturing CAR-T cells. After expansion of cells at the final manufacturing step, they are concentrated and transferred into an appropriate solvent depending on the desired application.

Therapeutic cells are stored in specialized media to prolong the viability of these cells either through refrigeration and or freezing processes. Such specialized media may not be compatible when the therapeutic cells are introduced into a patient. It may thus be helpful to both wash and concentrate the therapeutic cells in a buffer or wash media that is biocompatible with both the therapeutic cells and with the patient. These washing and concentration processes conventionally involve the use of centrifugation and physical filtration. The washing step may be repeated a number of times. For example, the specialized media (which can be pyrogenic or otherwise harmful) may be fully removed with multiple wash steps, and the cells may be suspended in a new buffer or wash solution. During this washing process, many of the cells are degraded or destroyed through the centrifugation and physical filtration processes. Moreover, the filtration process can be rather inefficient and may entail a non-sterile intrusion into the environment for batch processing, whereby the cell culture is exposed to possible pathogens or outside cellular influences that would be harmful to the target cell culture. Further yet, with these physical filtration processes, biological waste is generated through the use of multiple physical filters which may incur additional steps for proper disposal. The cost and timeliness of this process is also not conducive to a fast or low-cost process of preparing the cells for introduction to the patient.

BRIEF SUMMARY

The present disclosure provides methods and systems for replacing or augmenting conventional centrifugation and physical filtration processes along with the multiple washing steps with a simpler, lower cost, and more friendly process for particles such as therapeutic cells. The methods/processes can be performed in a sterile environment and in a continuous form.

Disclosed herein are methods of washing particles, which comprise feeding an initial mixture of a first media and the particles through a flow chamber of an acoustophoretic device. For example, the first media may contain preservatives such as dimethyl sulfoxide (DMSO) which are undesirable for future applications/uses of the particles, such as cells. The acoustophoretic device also comprises at least one ultrasonic transducer that includes a piezoelectric material that is configured to be driven to create a multi-dimensional acoustic standing wave in the flow chamber. The at least one ultrasonic transducer is driven to create a multi-dimensional acoustic standing wave in the flow chamber, such that at least a portion of the particles are trapped in the multi-dimensional acoustic standing wave. The trapped particles are subsequently mixed with a second media to wash the trapped particles (e.g. remove the first media from the particles).

In some embodiments, the initial mixture is run through the flow chamber to obtain an intermediate mixture of the particles in a reduced volume of the first media. The intermediate mixture is then collected, and mixed together with the second media to form a secondary mixture. The secondary mixture is then fed through the flow chamber to obtain a final mixture of particles in a reduced volume of the second media.

In other embodiments, the second media is fed into the flow chamber after the initial mixture is fed through the flow chamber. Here, the second media displaces the first media, or gradually replaces the first media.

In still other embodiments, the acoustophoretic device further comprises a collector located below the at least one ultrasonic transducer so that as the trapped particles form clusters and grow to a critical size and subsequently fall out of the multi-dimensional acoustic standing wave, the clusters fall into the collector. The collector leads to a collection container that contains the second media, mixing the clusters of particles together with the second media.

The second media can be a biocompatible wash or a buffer solution.

The particles may be cells. The cells may be Chinese hamster ovary (CHO) cells, NS0 hybridoma cells, baby hamster kidney (BHK) cells, human cells, regulatory T-cells, Jurkat T-cells, CAR-T cells, B cells, or NK cells, peripheral blood mononuclear cells (PBMCs), algae, plant cells, bacteria, or viruses. The cells may be attached to m icrocarriers.

Sometimes, the piezoelectric material of the at least one ultrasonic transducer is in the form of a piezoelectric array formed from a plurality of piezoelectric elements. Each piezoelectric element can be physically separated from surrounding piezoelectric elements by a potting material. The piezoelectric array can be present on a single crystal, with one or more channels separating the piezoelectric elements from each other. Each piezoelectric element can be individually connected to its own pair of electrodes. The piezoelectric elements can be operated in phase with each other, or operated out of phase with each other. The acoustophoretic device may further comprise a cooling unit for cooling the at least one ultrasonic transducer.

Also disclosed are methods of separating microcarriers from cells, comprising feeding an initial mixture of a first media and microcarriers with attached cells thereon through a flow chamber of an acoustophoretic device. Again, the acoustophoretic device also comprises at least one ultrasonic transducer including a piezoelectric material that is configured to be driven to create a multi-dimensional acoustic standing wave in the flow chamber. The at least one ultrasonic transducer is driven to create a multi-dimensional acoustic standing wave in the flow chamber, and to trap at least a portion of the microcarriers with attached cells in the multi-dimensional acoustic standing wave. The trapped microcarriers with attached cells are then washed by flowing a second media through the flow chamber to remove the first media. Next, a third media containing an enzyme is flowed through the flow chamber to separate the cells from the microcarriers.

In some examples, the microcarriers remain trapped in the multi-dimensional acoustic standing wave, and the cells are separated from the microcarriers and/or the fluid. Alternatively, the cells remain trapped in the multi-dimensional acoustic standing wave, and the microcarriers flow through the device. The mixture of the cells and the third media can then be recovered. The second media and the third media can be the same, or can be different. In particular embodiments, the enzyme is trypsin.

Also disclosed herein are culture bags, comprising: a sidewall that surrounds an internal volume, the internal volume including an upper portion and a lower portion; a fill port at an upper end of the culture bag in the upper portion; a drain port at a lower end of the culture bag in the lower portion; and a wash outlet located at a bottom end of the upper portion between the fill port and the drain port; wherein the upper portion may have a larger diameter than the lower portion.

The wash outlet may be connected to a wash inlet located in the lower portion of the culture bag. The lower portion may comprise from about 1% to about 5% of the internal volume.

Also disclosed are acoustophoretic systems that use the culture bag described above. The systems also include at least one ultrasonic transducer including a piezoelectric material that is configured to be driven to create a multi-dimensional acoustic standing wave in the culture bag; and means for moving the at least one ultrasonic transducer relative to the culture bag between the upper end and the lower end thereof.

The acoustophoretic system may further comprise a tank into which the culture bag can be placed. The means for moving the at least one ultrasonic transducer may be a conveyor system located outside of the tank.

The acoustophoretic system may further comprise means for sealing the culture bag between the upper portion and the lower portion thereof. For example, a heating bar could be used to melt two opposite sides of the culture bag together, separating the upper portion from the lower portion.

Also disclosed herein are acoustophoretic systems, comprising: an acoustophoretic device comprising a feed port, a drain port located below the feed port and configured to operate as both a wash inlet and a concentrate outlet, a wash outlet, and at least one ultrasonic transducer including a piezoelectric material that is configured to be driven to create a multi-dimensional acoustic standing wave; a feed line leading to the feed port of the acoustophoretic device; a waste line leading away from the waste outlet of the acoustophoretic device; and a wash line leading to the drain port of the acoustophoretic device; and a concentrate line leading away from the drain port of the acoustophoretic device. The various lines lead to containers that provide or receive various materials to/from the acoustophoretic device.

The acoustophoretic system can further comprise a valve to switch between the wash line and the concentrate line.

Alternatively, in the acoustophoretic system, the feed line and the wash line can pass through an inflow selector valve. The acoustophoretic system may further comprise a feed selector valve upstream of the inflow selector valve. The waste line and the concentrate line can also pass through an outflow selector valve.

These and other non-limiting characteristics are more particularly described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the example embodiments disclosed herein and not for the purposes of limiting the same.

FIG. 8 is a conventional single-piece monolithic piezoelectric material used in an ultrasonic transducer.

FIG. 9 is an example rectangular piezoelectric array having 16 piezoelectric elements used in the transducers of the present disclosure.

FIG. 10 is another example rectangular piezoelectric array having 25 piezoelectric elements used in the transducers of the present disclosure.

FIG. 11 is a diagram illustrating a piezoelectric material having 16 piezoelectric elements operated in out-of-phase modes. Dark elements indicate a 0° phase angle and light elements indicate a 180° phase angle.

FIG. 12 illustrates a kerfed piezoelectric material (top) versus a transducer array that has piezoelectric elements joined together by a potting material (bottom).

FIG. 22 shows a microscopic image of the microcarriers with T attached cells in the feed and during the three wash passes, and the concentration of separated microcarriers and T cells in the permeate.

DETAILED DESCRIPTION

Figure 1:
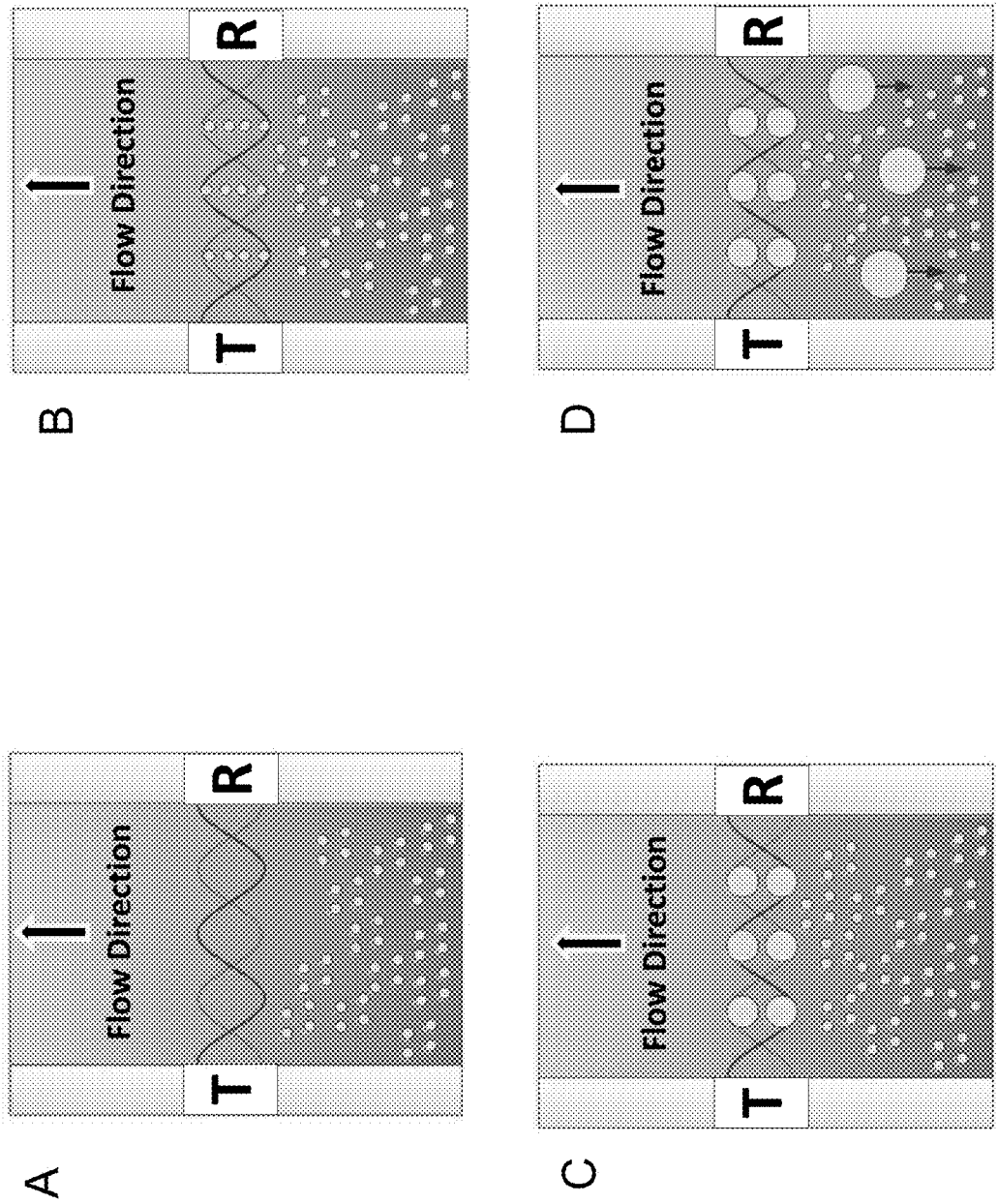
FIG. 1 illustrates an example acoustophoresis process using a transducer and reflector to create an acoustic standing wave for trapping particles and separating them from a fluid by enhanced gravitational settling.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, e.g. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, e.g. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, e.g. ground level. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least 1 and less than 10.

The acoustophoretic technology of the present disclosure employs acoustic standing waves to concentrate, wash, and/or separate materials (such as particles or a secondary fluid) in a primary or host fluid. In particular, as shown in the upper left image (A) of FIG. 1, an ultrasonic transducer T creates an acoustic wave in the fluid, which interacts with a reflector R positioned across from the ultrasonic transducer to create an acoustic standing wave. Although a reflector R is illustrated in FIG. 1, another transducer may be used to reflect and/or generate acoustic energy to form the acoustic standing wave.

As shown in the upper right image (B) of FIG. 1, as the host fluid and material entrained in the host fluid flows upwards through the acoustic standing wave, the acoustic standing wave(s) traps (retains or holds) the material (e.g., secondary phase materials, including fluids and/or particles). The scattering of the acoustic field off the material results in a three-dimensional acoustic radiation force, which acts as a three-dimensional trapping field.

The three-dimensional acoustic radiation force generated in conjunction with an ultrasonic standing wave is referred to in the present disclosure as a three-dimensional or multi-dimensional standing wave. The acoustic radiation force is proportional to the particle volume (e.g. the cube of the radius) of the material when the particle is small relative to the wavelength. The acoustic radiation force is proportional to frequency and the acoustic contrast factor. The acoustic radiation force scales with acoustic energy (e.g. the square of the acoustic pressure amplitude). For harmonic excitation, the sinusoidal spatial variation of the force drives the particles to the stable positions within the standing waves. When the acoustic radiation force exerted on the particles is stronger than the combined effect of fluid drag force and buoyancy and gravitational force, the particle can be trapped within the acoustic standing wave field, as shown in the upper right image (B) of FIG. 1.

As can be seen in the lower left image (C) of FIG. 1, this trapping results in coalescing, clumping, aggregating, agglomerating, and/or clustering of the trapped particles.

Additionally, secondary inter-particle forces, such as Bjerkness forces, aid in particle agglomeration.

As the particles continue to coalesce, clump, aggregate, agglomerate, and/or cluster the particles can grow to a certain size at which gravitational forces on the particle cluster overcome the acoustic radiation force. At such size, the particle cluster can fall out of the acoustic standing wave, as shown in the lower right image (D) of FIG. 1.

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. A planar or one-dimensional acoustic standing wave may provide acoustic forces in the axial or wave propagation direction. The lateral force in planar or one-dimensional acoustic wave generation may be two orders of magnitude smaller than the axial force. The multi-dimensional acoustic standing wave may provide a lateral force that is significantly greater than that of the planar acoustic standing wave. For example, the lateral force may be of the same order of magnitude as the axial force in the multi-dimensional acoustic standing wave.

The acoustic standing waves of the present disclosure can be used to trap particles (e.g. therapeutic cells such as T cells, B cells, NK cells) suspended in a first media in the standing wave. The first media can then be replaced with a second media (e.g., a biocompatible wash or buffer solution). Put another way, the host fluid of the particles can be replaced. Prior to replacing the first media with the second media, acoustophoresis can be used to perform a diafiltration process, as shown in FIG. 2.

Figure 2:
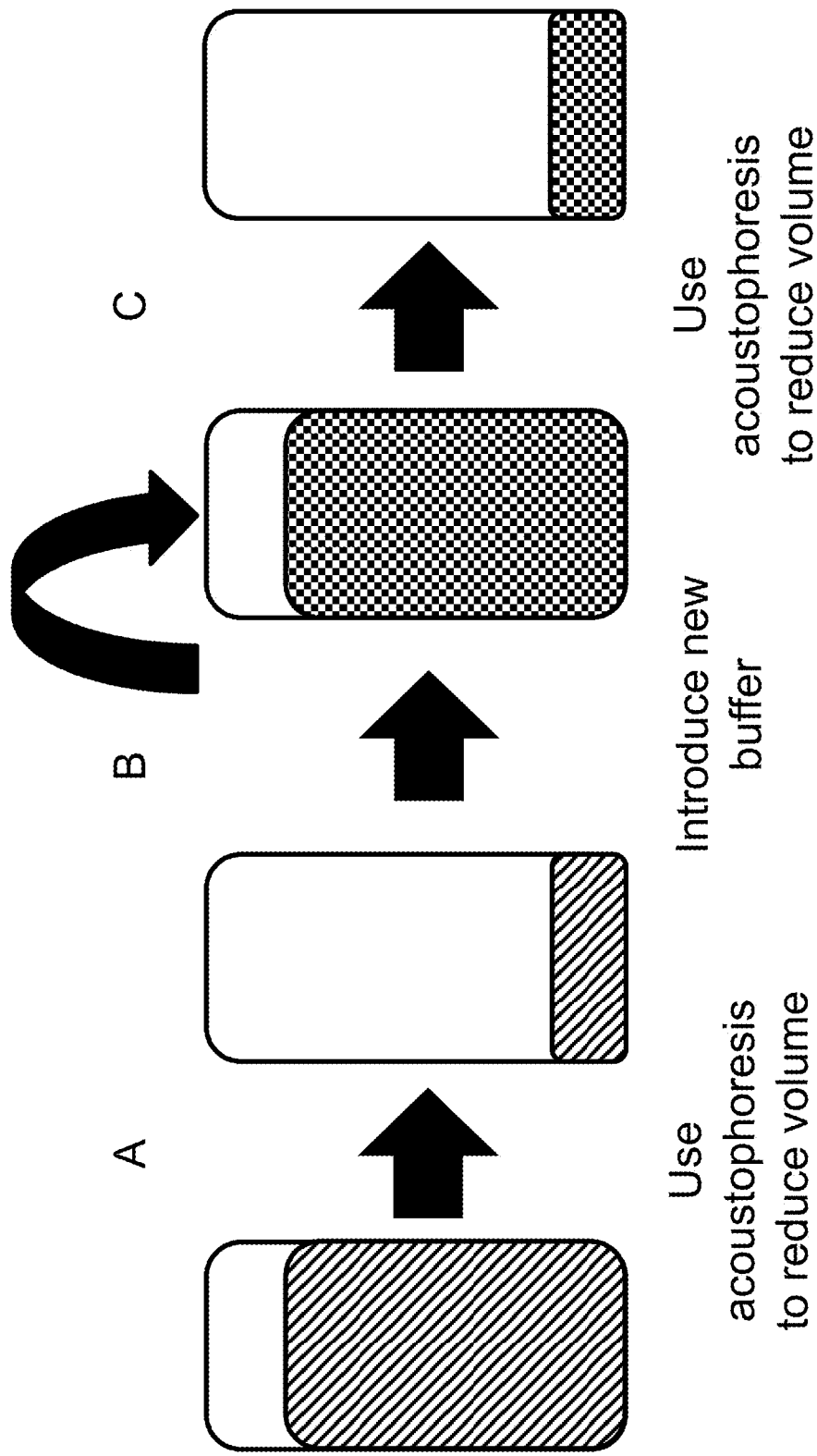
FIG. 2 illustrates an example cell concentration and washing process ("diafiltration") according to the present disclosure using acoustophoresis.

In FIG. 2, starting with an initial mixture that has a low cell density of, for example, less than $1 \times 10^6$ cells/mL, acoustophoresis can be used to reduce the volume of the initial mixture, for example by at least 10×, including 20× and up to 100× or more. The cell concentration may be increased by at least 10×, including 20× and up to 100× or more. This initial reduction process is the first volume reduction step (A). Next, the second media (e.g., a biocompatible wash or buffer solution) can be introduced to at least partially displace the first media, as indicated in step (B). Next, the new mixture of the cells and second media can be subjected to an acoustophoretic volume reduction step (C). This series of operations is referred to as a "diafiltration" process.

Figure 3:
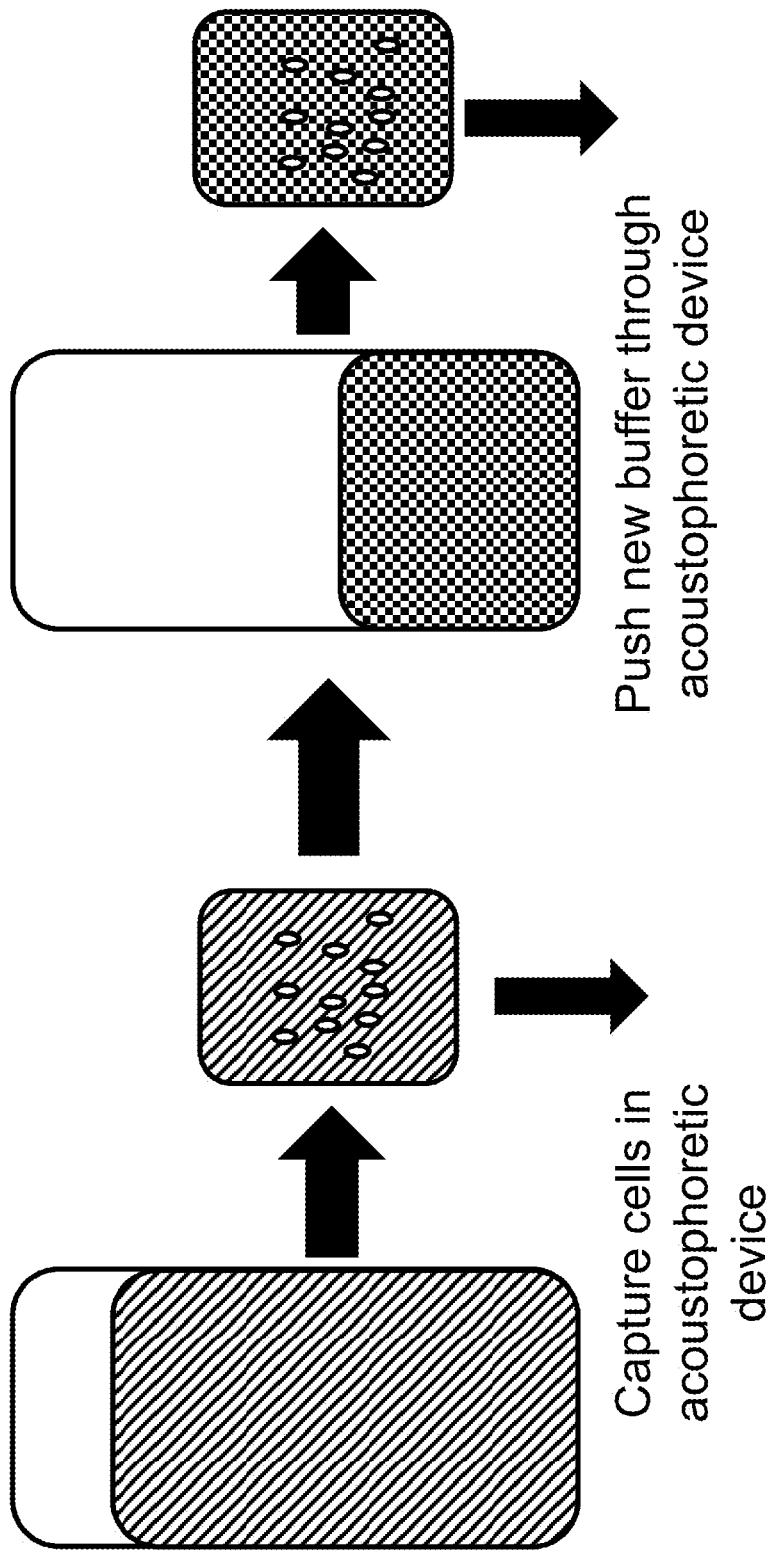
FIG. 3 illustrates another example cell concentration and washing process (push through) according to the present disclosure using acoustophoresis.

FIG. 3 illustrates a single-step, push-through process in which particles/cells are trapped in the acoustic standing wave and held in the acoustophoretic device. The second media (e.g., a biocompatible wash or buffer solution) is then flowed into the acoustophoretic device to effectively "wash out" the first media. With the push-through process, more than 90%, including up to 99% or more, of the first media can be removed from the particles/cells. The push-through process can be employed as a continuous, single-use process that uses less buffer solution and less time than the diafiltration process of FIG. 2.

Figure 4:
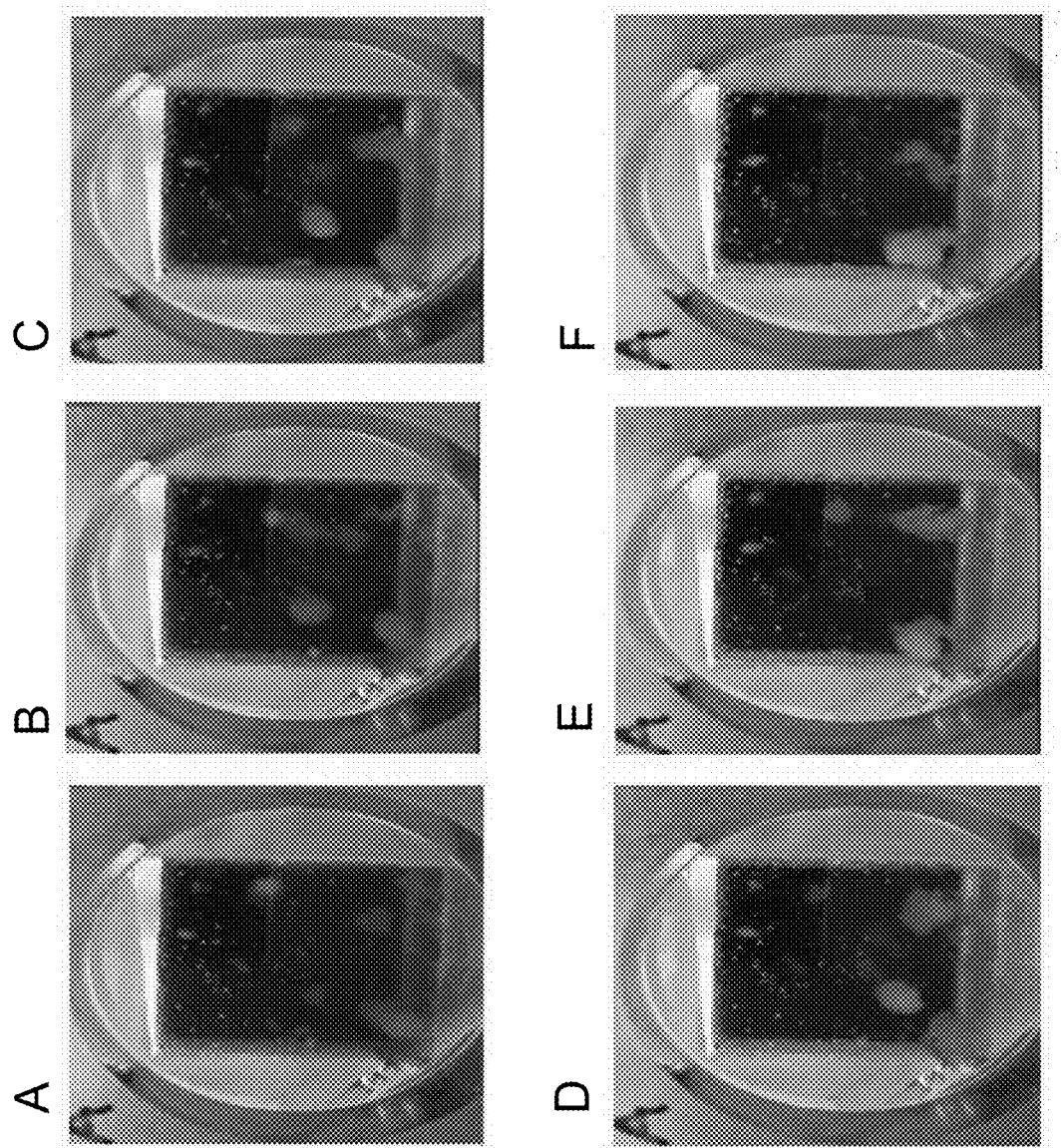
FIG. 4 shows six photographs that, from left to right and top to bottom, show the progression of cells being trapped in an acoustophoretic device before a second media mixture (dyed blue) is flowed into the device and gradually replaces the first media (dyed red).

FIG. 4 shows six photographs that, from left to right and top to bottom, show the progression of cells being trapped in an acoustophoretic device before a second media mixture (dyed blue) is flowed into the device and gradually replaces the first media (dyed red). In FIG. 4, a 150 mL feed volume was used with 80 mL of electroporation media wash for the second media. The concentrate was drawn off at a flow rate of 10 mL/minute. As can be seen in these pictures, over time the first media is replaced with the second media.

Figure 5:
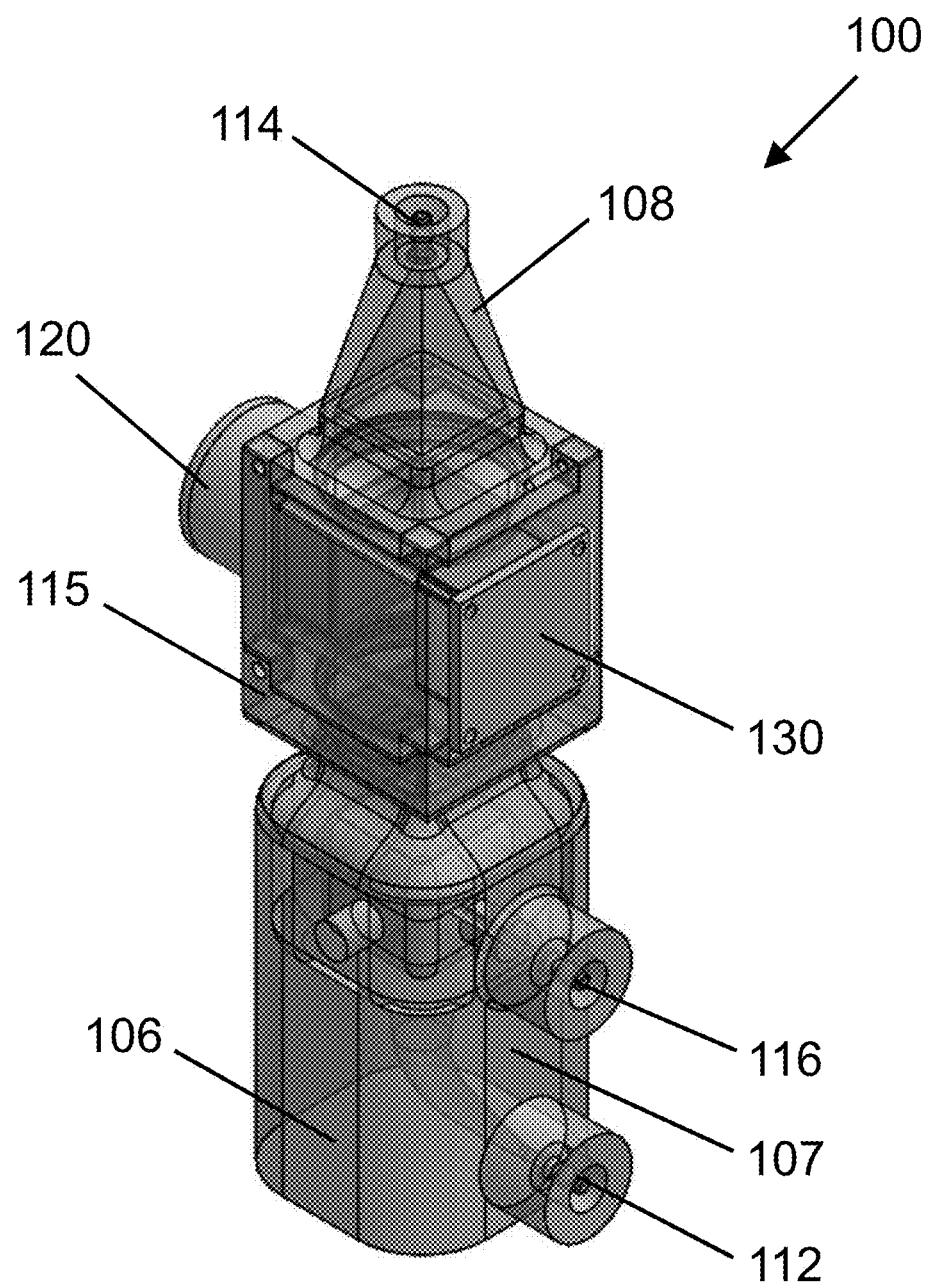
FIG. 5 is a perspective view of an example acoustophoretic device according to the present disclosure.
Figure 6:
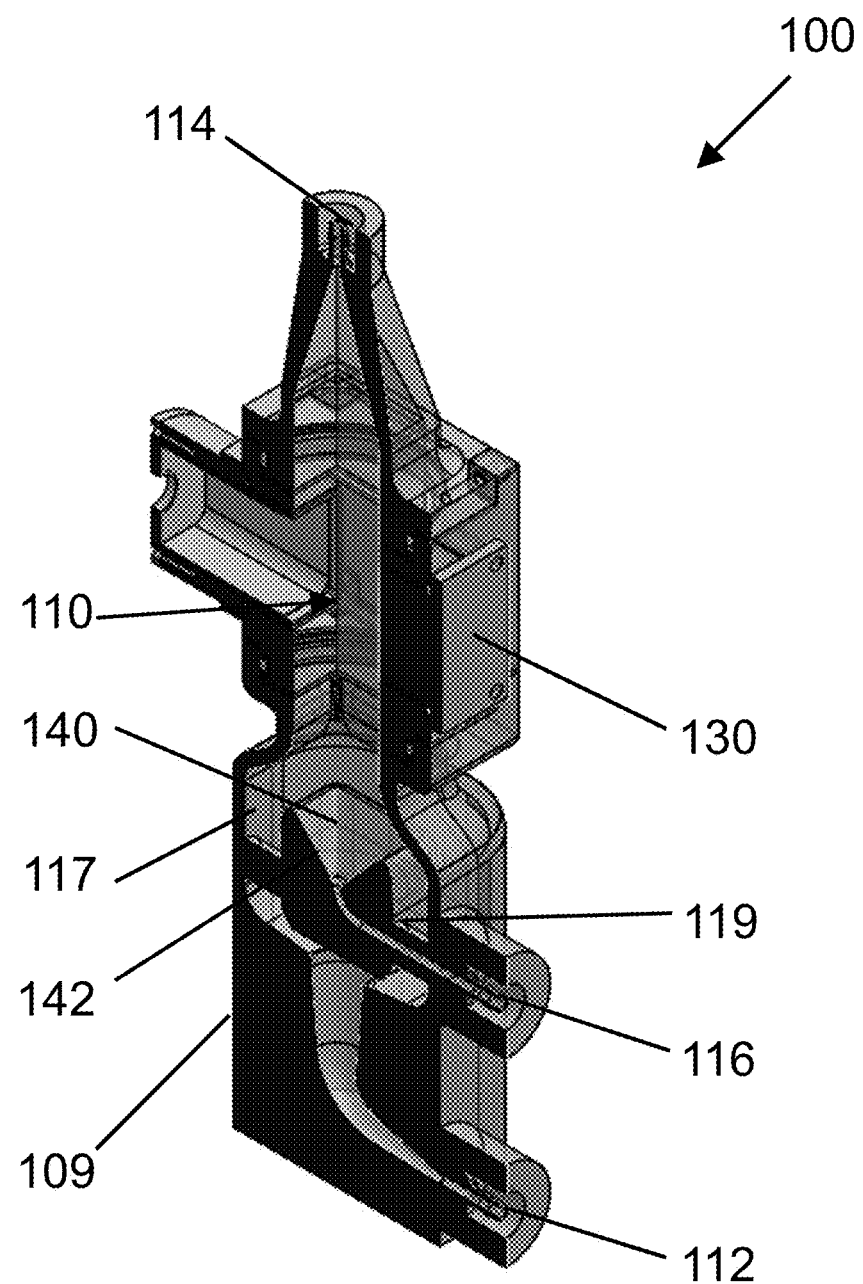
FIG. 6 is a cross-sectional illustration of the acoustophoretic device of FIG. 5.

With reference now to FIG. 5 and FIG. 6, a first example embodiment of an acoustophoretic device 100 for separation of particles/cells from fluid is depicted. The acoustophoretic device 100 includes a flow chamber 110 having at least one inlet and at least one outlet. In this embodiment, the flow chamber 110 includes inlet 112, permeate outlet 114, concentrate outlet 116, an ultrasonic transducer 120, and a reflector 130. The inlet 112 can, in certain embodiments, serve the dual function of introducing the cells surrounded by the first media into the flow chamber 110 in addition to introducing the second media into the flow chamber 110. Alternatively, separate inlets can be used for introducing the first and second media.

The flow chamber 110 is the region of the device 100 through which is flowed the cells surrounded by the first media. In this embodiment, the flow chamber 110 is defined by inlet 112, permeate outlet 114, and concentrate outlet 116. The flow chamber 110 is further defined by a sidewall 115 to which the ultrasonic transducer 120 and the reflector 130 are coupled. As seen here, the sidewall is shaped so that the ultrasonic transducer and reflector are located on opposite sides thereof.

Inlet 112 is located at a first end 106 of the flow chamber 110. In particular embodiments, the ingress of material through the inlet 112 can be configured to occur toward the bottom end of the inlet 112, such that the inflow of fluid into the flow chamber 110 occurs closer to the bottom end of the flow chamber 110 than the top end thereof.

As depicted in FIG. 5 and FIG. 6, the inlet 112 is located along a first side 107 of the device 100. The first side 107 of the device also houses the reflector 130, while a second side 109 of the device, opposite the first side thereof, houses the ultrasonic transducer 120. The inlet 112 could alternatively be located along the second side 109 of the device (e.g., on the same side as the ultrasonic transducer) or on another side of the device.

In the embodiment depicted in FIG. 5, the permeate outlet 114 is located at a second end 108 of the flow chamber 100. The permeate outlet 114 is generally used to recover the first media and residual cells from the flow chamber 110. In comparison, the concentrate outlet 116 is located between the inlet 112 and the permeate outlet 114, below the ultrasonic transducer 120 and the reflector 130. The concentrate outlet 116 is generally configured to recover the cells from the flow chamber 110. In certain embodiments, however, it may be desired to recover other material (e.g., microcarriers) from the device, in which case the microcarriers can be recovered by the concentrate outlet and the cells can be recovered via the permeate outlet along with the media). As seen here, the permeate outlet 114 is generally located above the ultrasonic transducer 120 and the reflector 130, while and the concentrate outlet 116 is generally located below the ultrasonic transducer 120 and the reflector 130.

In the embodiment depicted in FIG. 5 and FIG. 6, the device 100 is vertically oriented, such that the first end 106 of the device is the bottom end thereof and the second end 108 of the device is the top end thereof. In this way, the cells surrounded by the first media is introduced at the bottom end of the device 100 and flows vertically upwards through the flow chamber from the inlet 112 toward the permeate outlet 114.

As can be best seen in FIG. 6, the device 100 also includes a collector 140. The collector 140 is located in the flow chamber 110 between the inlet 112 and the ultrasonic transducer 120 and the reflector 130. The collector 140 is located above the concentrate outlet 116 and, in particular, is defined by angled walls 142 that lead to the concentrate outlet 116. Put another way, the collector 140 leads into a common well defined by angled walls 142 that taper downwards in cross-sectional area (i.e. larger area to smaller area) to a vertex at the bottom of the collector, which is fluidically connected to and drains off one side into the concentrate outlet 116 via flowpath 119. In this way, the multi-dimensional acoustic standing wave can direct the concentrated cells to the collector 140 for collection and removal from the flow chamber 110 via the concentrate outlet 116. An annular plenum 117 surrounds the collector 140, permitting the mixture of host fluid/cells to flow from the inlet 112 around the collector 140 into the flow chamber 110.

In some embodiments, the collector leads to a collection container that is filled with the second media. In this way, the second media is not flowed through the flow chamber of the device. Instead, as the cells are trapped in the acoustic standing wave and form clusters that grow to a critical size and subsequently fall out of the multi-dimensional acoustic standing wave, the cell clusters fall into the collector and are led to the collection container. The collection container can be separable from the rest of the device.

As seen here, preferably, fluid flows through the device upwards. The cells surrounded by the first media enters the device through inlet 112 at a bottom end of the device and then makes a sharp turn to flow upwards. This change in direction desirably reduces turbulence, producing near plug flow upwards through the device. Flow continues upwards through the annular plenum 117 and up into the flow chamber 110. There, the cells encounter the multi-dimensional acoustic standing wave(s), which traps the cells, as explained herein. Concentration of the cells occurs within the acoustic standing wave(s), which can also cause coalescence, clumping, aggregation, agglomeration and/or clustering of the cells.

As the cells are concentrated, they eventually overcome the combined effect of the fluid flow drag forces and acoustic radiation force, and they fall downwards into collector 140. They can then be flowed through flowpath 119 and collected at concentrate outlet 116. A much higher number of cells is obtained in a smaller volume (i.e., the target cells are concentrated).

Figure 7:
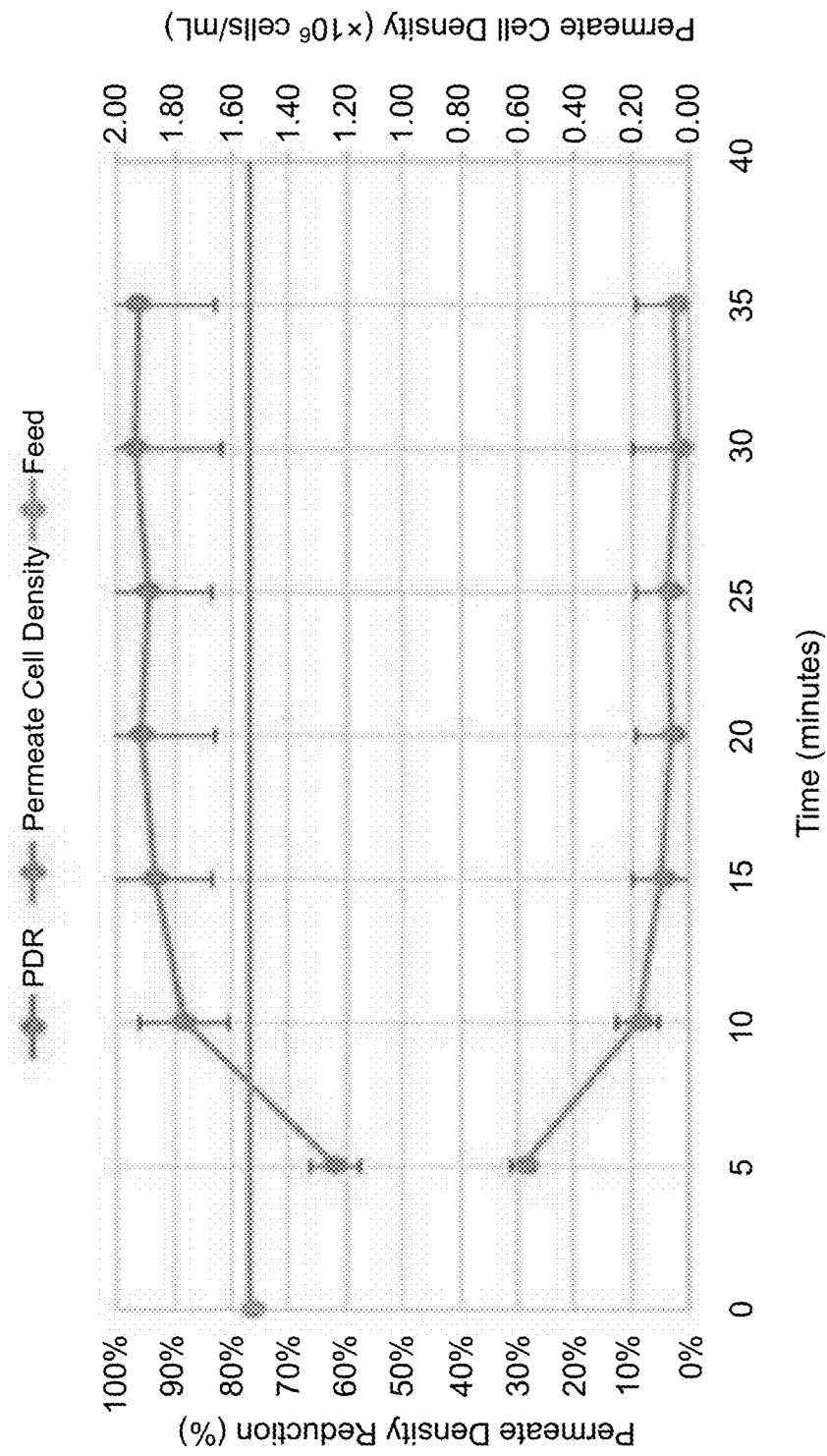
FIG. 7 is a graph showing the performance of the acoustophoretic device of FIG. 5. The x-axis is elapsed time (minutes) and runs from 0 to 40 in increments of 5. The left-side y-axis is permeate density reduction (%) and runs from 0 to 100 in increments of 10. The right-side y-axis is permeate cell density ($\times 10^6$ cells/mL) and runs from 0.00 to 2.00 in increments of 0.20. The uppermost solid line represents permeate reduction density (%). The lowermost solid line represents permeate cell density. The middle line running substantially horizontally across the page represents feed cell density for reference purposes.

FIG. 7 is a graph showing the performance of the acoustophoretic device of FIG. 5. The device was operated at a fixed frequency of 2.234 MHz for a mixture having a feed cell density of about $1.5 \times 10^6$ cells/mL. As can be seen, the device achieved a permeate density reduction (PDR) of greater than 95% over about 35 minutes and a permeate cell density of less than $0.10 \times 10^6$ cells/mL over the same time period.

The piezoelectric transducer(s) of the acoustophoretic devices and systems of the present disclosure can be single monolithic piezoelectric materials or can be made from an array of piezoelectric materials. The piezoelectric material can be a ceramic material, a crystal or a polycrystal, such as PZT-8 (lead zirconate titanate). FIG. 8 shows a monolithic, one-piece, single electrode piezoelectric crystal 200. The piezoelectric crystal has a substantially square shape, with a length 203 and a width 205 that are substantially equal to each other (e.g. about one inch). The crystal 200 has an inner surface 202, and the crystal also has an outer surface 204 on an opposite side of the crystal which is usually exposed to fluid flowing through the acoustophoretic device. The outer surface and the inner surface are relatively large in area, and the crystal is relatively thin (e.g. about 0.040 inches for a 2 MHz crystal).

FIG. 9 shows a piezoelectric crystal 200' made from an array of piezoelectric materials. The inner surface 202 of this piezoelectric crystal 200' is divided into a piezoelectric array 206 with a plurality of (i.e. at least two) piezoelectric elements 208. However, the array is still a single crystal. The piezoelectric elements 208 are separated from each other by one or more channels or kerfs 210 in the inner surface 202. The width of the channel (i.e. between piezoelectric elements) may be on the order of from about 0.001 inches to about 0.02 inches. The depth of the channel can be from about 0.001 inches to about 0.02 inches. In some instances, a potting material 212 (e.g., epoxy, Sil-Gel, and the like) can be inserted into the channels 210 between the piezoelectric elements. The potting material 212 is non-conducting, acts as an insulator between adjacent piezoelectric elements 208, and also acts to hold the separate piezoelectric elements 208 together. Here, the array 206 contains sixteen piezoelectric elements 208 (although any number of piezoelectric elements is possible), arranged in a rectangular 4×4 configuration (square is a subset of rectangular). Each of the piezoelectric elements 208 has substantially the same dimensions as each other. The overall array 200' has the same length 203 and width 205 as the single crystal illustrated in FIG. 8.

FIG. 10 shows another embodiment of a transducer 200". The transducer 200" is substantially similar to the transducer 200' of FIG. 9, except that the array 206 is formed from twenty-five piezoelectric elements 208 in a 5x5 configuration. Again, the overall array 200" has the same length 203 and width 205 as the single crystal illustrated in FIG. 8.

Each piezoelectric element in the piezoelectric array of the present disclosure may have individual electrical attachments (e.g. electrodes), so that each piezoelectric element can be individually controlled for frequency and power. These elements can share a common ground electrode. This configuration allows for not only the generation of a multi-dimensional acoustic standing wave, but also improved control of the acoustic standing wave. In this way, it is possible to drive individual piezoelectric elements (or multiple, separate ultrasonic transducers) with arbitrary phasing and/or different or variable frequencies and/or in various out-of-phase modes. For example, FIG. 11 illustrates an exemplary 0-180-0-180 mode, though additional modes can be employed as desired, such as a 0-180-180-0 mode. For example, for a 5x5 array, additional modes can be employed as desired, such as a 0-180-0-180-0 mode, a 0-0-180-0-0 mode, a 0-180-180-180-0 mode, or a 0-90-180-90-0 mode. The array could also be driven, for example, such that a checkerboard pattern of phases is employed, such as is shown in FIG. 11. In summary, a single ultrasonic transducer that has been divided into an ordered array can be operated such that some components of the array are out of phase with other components of the array.

The piezoelectric array can be formed from a monolithic piezoelectric crystal by making cuts across one surface so as to divide the surface of the piezoelectric crystal into separate elements. The cutting of the surface may be performed through the use of a saw, an end mill, or other means to remove material from the surface and leave discrete elements of the piezoelectric crystal between the channels/grooves that are thus formed.

As explained above, a potting material may be incorporated into the channels/grooves between the elements to form a composite material. For example, the potting material can be a polymer, such as epoxy. In particular embodiments, the piezoelectric elements 208 are individually physically isolated from each other. This structure can be obtained by filling the channels 210 with the potting material, then cutting, sanding or grinding the outer surface 204 down to the channels. As a result, the piezoelectric elements are joined to each other through the potting material, and each element is an individual component of the array. Put another way, each piezoelectric element is physically separated from surrounding piezoelectric elements by the potting material. FIG. 12 is a cross-sectional view comparing these two embodiments. On top, a crystal as illustrated in FIG. 9 is shown. The crystal is kerfed into four separate piezoelectric elements 208 on the inner surface 202, but the four elements share a common outer surface 204. On the bottom, the four piezoelectric elements 208 are physically isolated from each other by potting material 212. No common surface is shared between the four elements.

Figure 13:
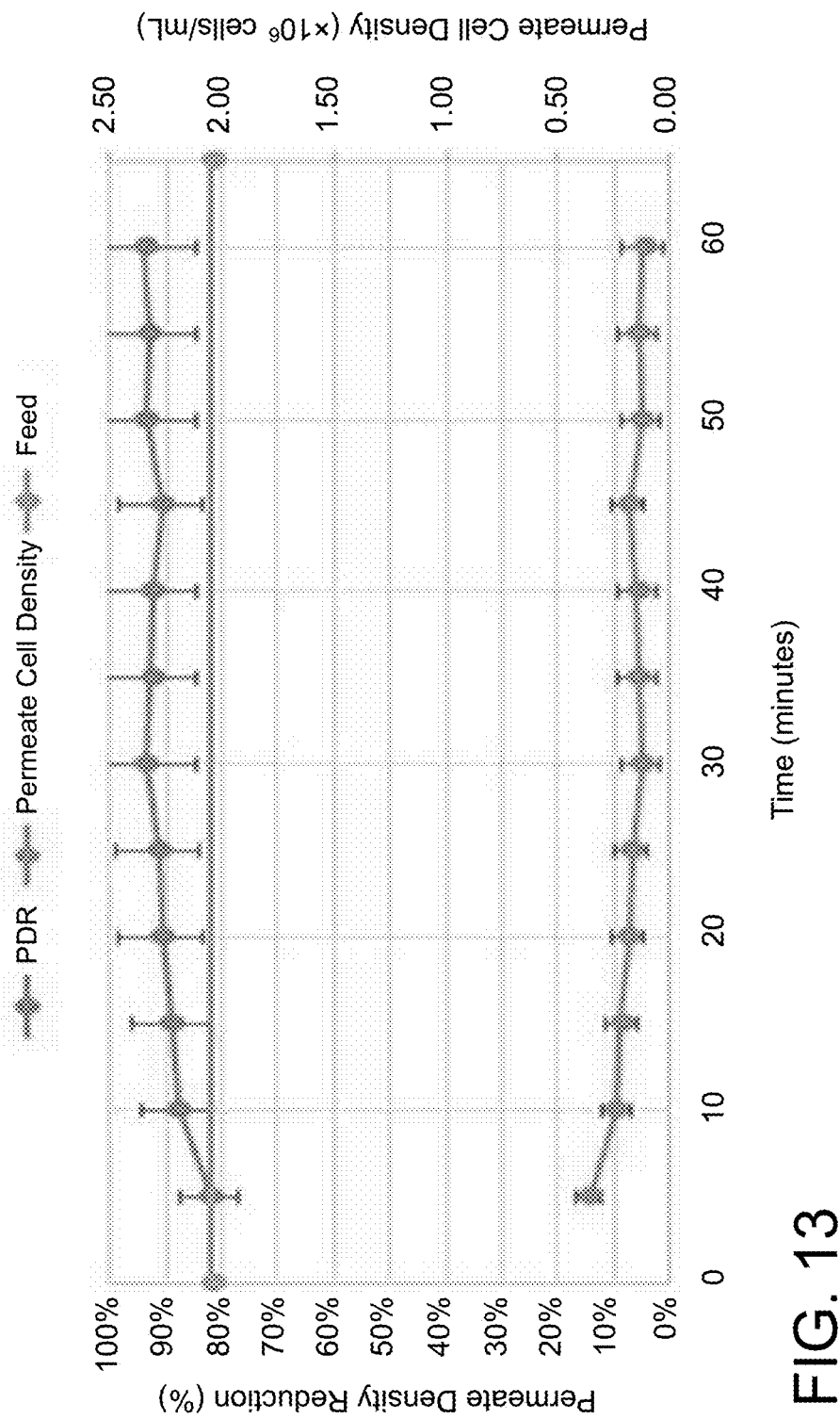
FIG. 13 is a graph showing the performance of an acoustophoretic device according to the present disclosure having a 16-element piezoelectric array, with the elements operated in-phase with one another. The x-axis is elapsed time (minutes) and runs from 0 to 60 in increments of 10. The left-side y-axis is permeate density reduction (%) and runs from 0 to 100 in increments of 10. The right-side y-axis is permeate cell density ($\times 10^6$ cells/mL) and runs from 0.00 to 2.50 in increments of 0.50. The uppermost solid line represents permeate reduction density (%). The lowermost solid line represents permeate cell density. The middle line running substantially horizontally across the page represents feed cell density for reference purposes.

FIG. 13 is a graph showing the performance of an acoustophoretic device according to the present disclosure having a 16-element piezoelectric array. The piezoelectric array was operated at a fixed frequency of 2.244 MHz for a mixture having a feed cell density of about $2.00 \times 10^6$ cells/mL. As can be seen, the device achieved a permeate density reduction (PDR) of about 95% over about 60 minutes and a permeate cell density of about $0.10 \times 10^6$ cells/mL over the same time period.

Figure 14:
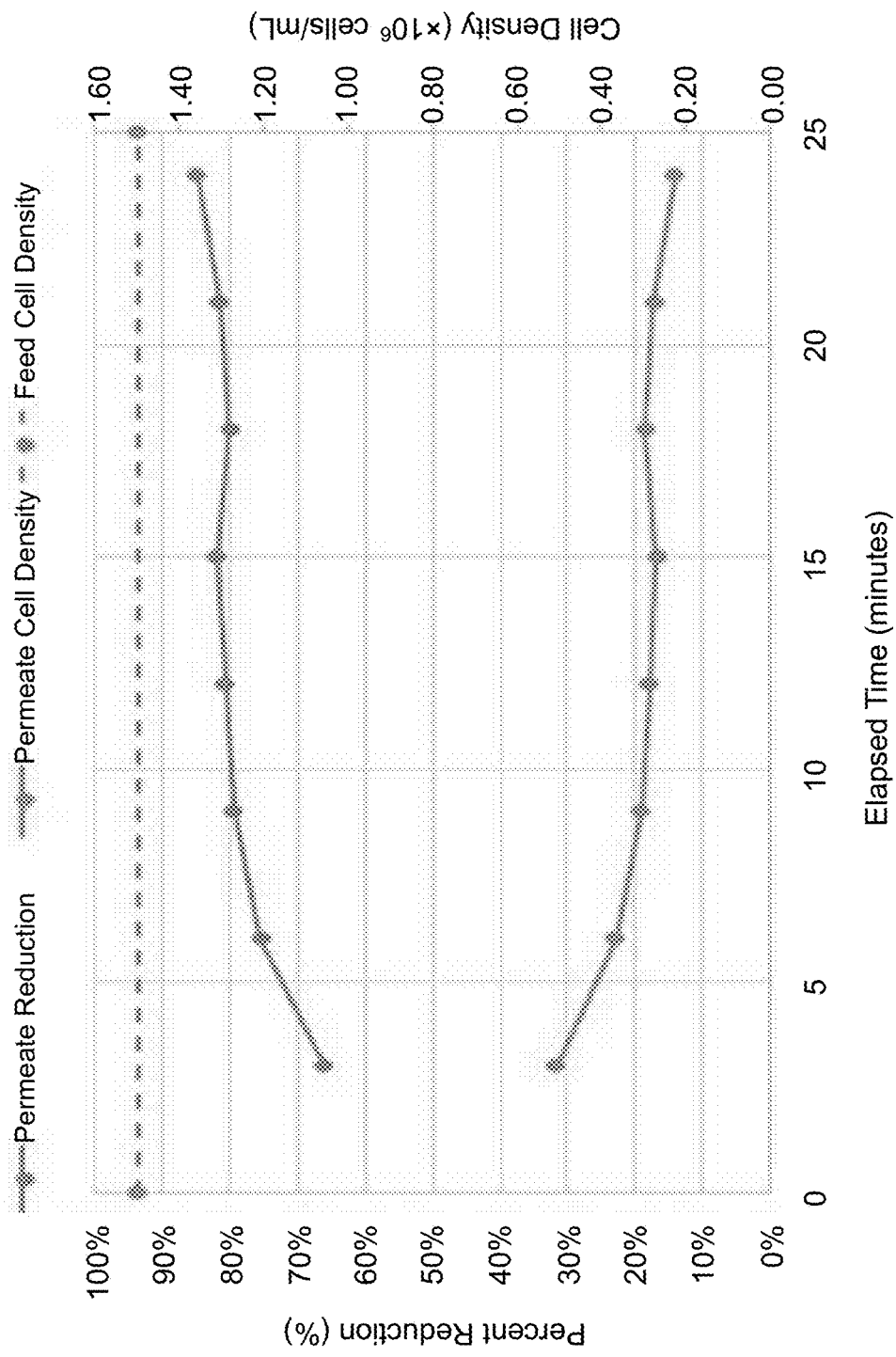
FIG. 14 is a graph showing the T-cell concentration performance of an acoustophoretic process according to the present disclosure with a low cell density culture. The x-axis is elapsed time (minutes) and runs from 0 to 25 in increments of 5. The left-side y-axis is percent reduction (%) and runs from 0 to 100 in increments of 10. The right-side y-axis is cell density ($\times 10^6$ cells/mL) and runs from 0.00 to 1.60 in increments of 0.20. The upper solid line represents permeate reduction (%). The lower solid line represents permeate cell density. The dashed line represents feed cell density for reference purposes.

The concentration efficiency of the acoustophoretic device was tested. First, a T-cell suspension having a cell density of $1 \times 10^6$ cells/mL was used. A feed volume of between about 500 and 1000 mL was used at a flow rate of 10-15 mL/minute. The results are graphically depicted in FIG. 14. The device exhibited a concentration factor of between 10× and 20×, a 90% cell recovery, and a 77% washout efficiency (i.e., the amount of the first media that was displaced by the second media) over ten minutes of testing. A 10° C. temperature increase was observed.

Figure 15:
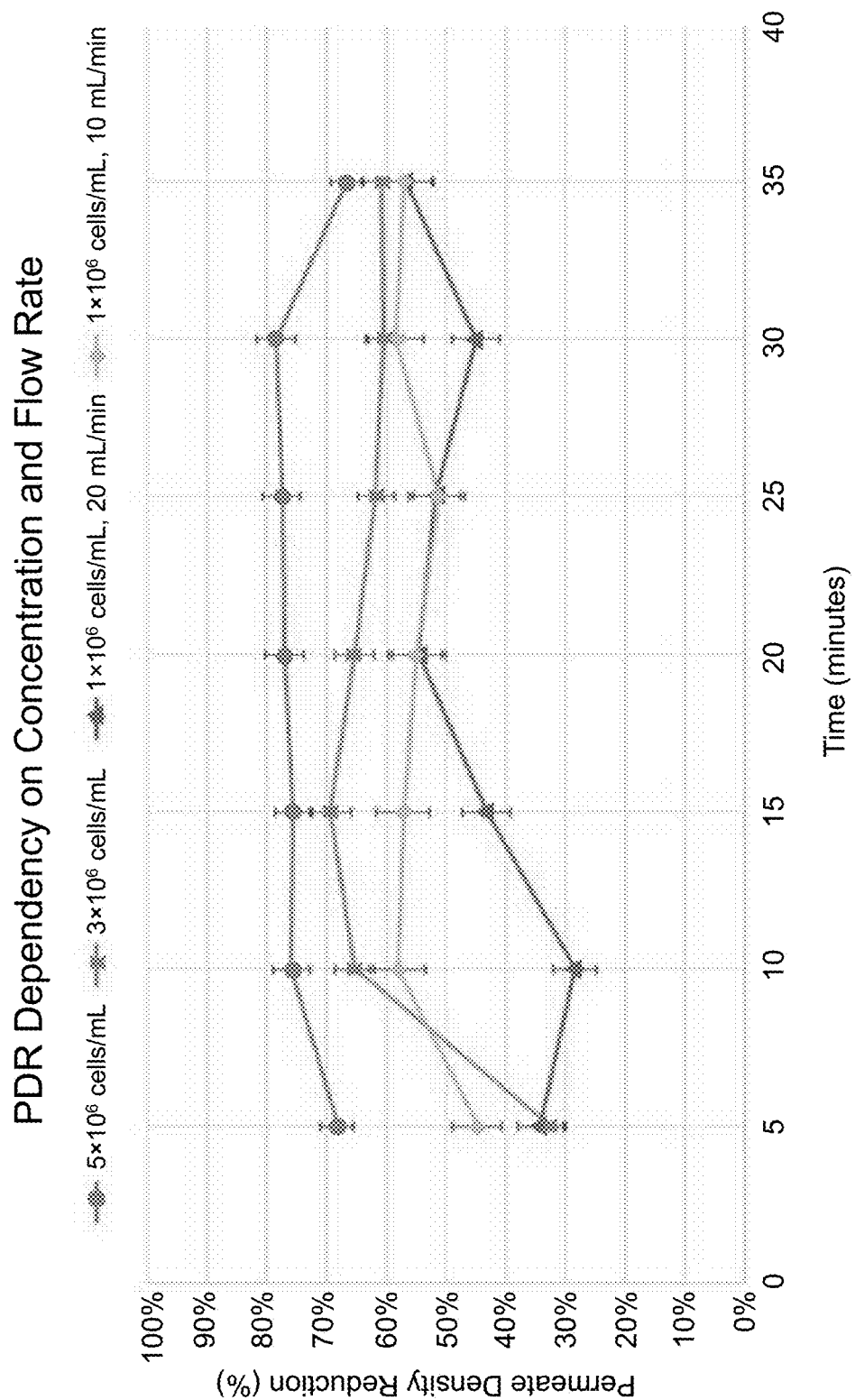
FIG. 15 is a graph showing the percent density reduction (PDR) dependency on concentration and flow rate for an acoustophoretic process according to the present disclosure. The x-axis is time (minutes) and runs from 0 to 40 in increments of 5. The y-axis is permeate density reduction (%) and runs from 0 to 100 in increments of 10. The line having circle-shaped data points represents a mixture having an initial cell concentration of $5\times10^6$ cells/mL. The line having x-shaped data points represents a mixture having an initial cell concentration of $3\times10^6$ cells/mL. The line having triangle-shaped data points represents a mixture having an initial cell concentration of $1\times10^6$ cells/mL at a flow rate of 20 mL/minute. The line having diamond-shaped data points represents a mixture having an initial cell concentration of $1\times10^6$ cells/mL at a flow rate of 10 mL/minute.

A yeast mixture was then used to test the dependency of the percent density reduction (PDR) on concentration and flow rate. The results are graphically depicted in FIG. 15. As seen here, the higher initial cell concentrations generally resulted in a greater PDR. Additionally, the varied flow rate (from 20 mL/min to 10 mL/min) did not have an observed effect on the PDR.

Figure 16:
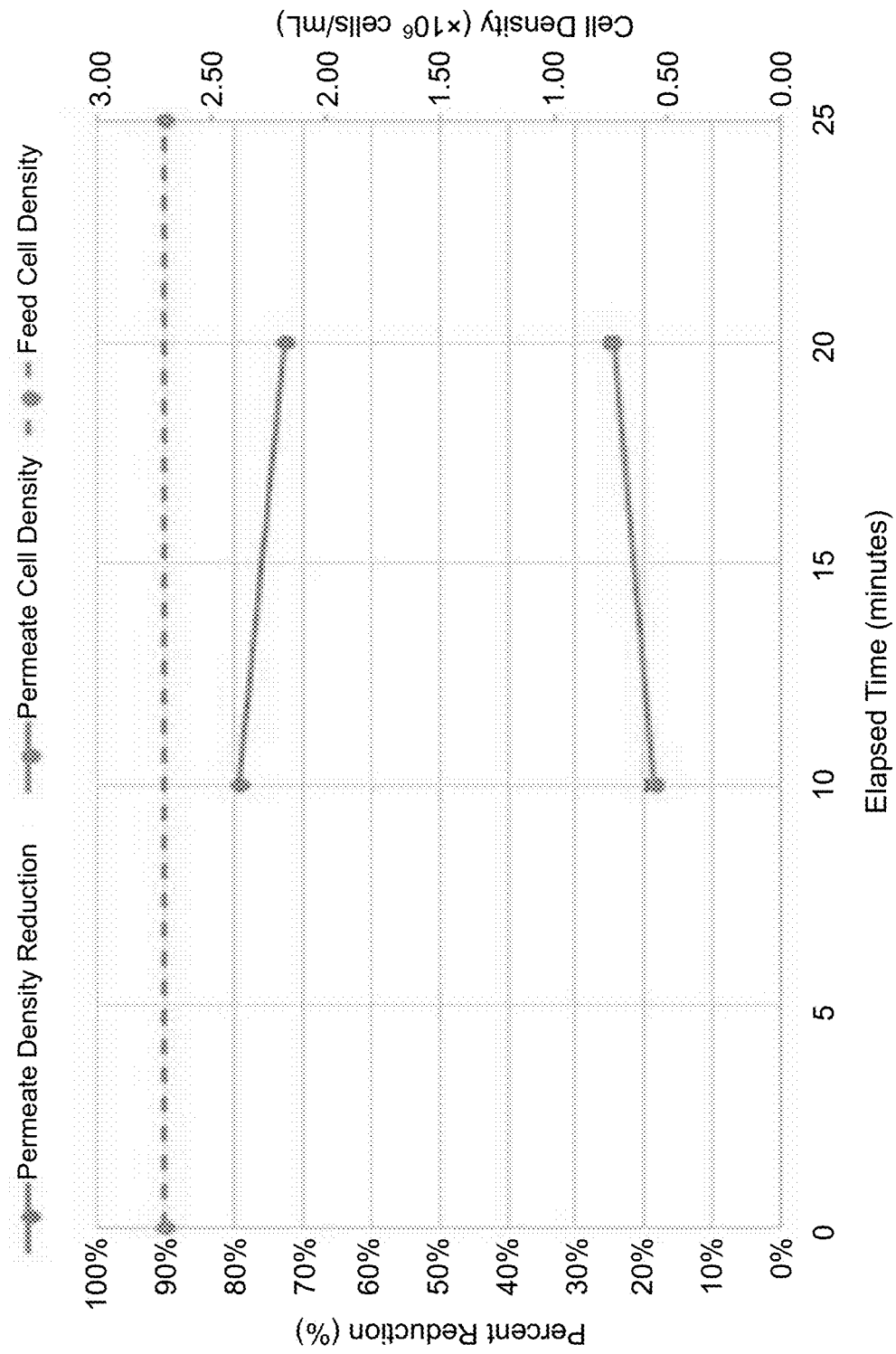
FIG. 16 is a graph showing the T-cell performance for an acoustophoretic process according to the present disclosure with a high cell density culture. The x-axis is elapsed time (minutes) and runs from 0 to 25 in increments of 5. The left-side y-axis is percent reduction (%) and runs from 0 to 100 in increments of 10. The right-side y-axis is cell density ($\times 10^6$ cells/mL) and runs from 0.00 to 3.00 in increments of 0.50. The upper solid line represents permeate density reduction (%). The lower solid line represents permeate cell density. The dashed line represents feed cell density for reference purposes.

The concentration efficiency of the acoustophoretic device was again tested with a higher cell density. A T-cell suspension having a cell density of 5×106 cells/mL was used. A feed volume of 1000 mL was used at a flow rate of 10-15 mL/minute. The results are graphically depicted in FIG. 16. The device exhibited a concentration factor of better than 10×, a 90% cell recovery, and a 77% washout efficiency over one hour of testing. A 10° C. temperature increase was again observed.

Figure 17:
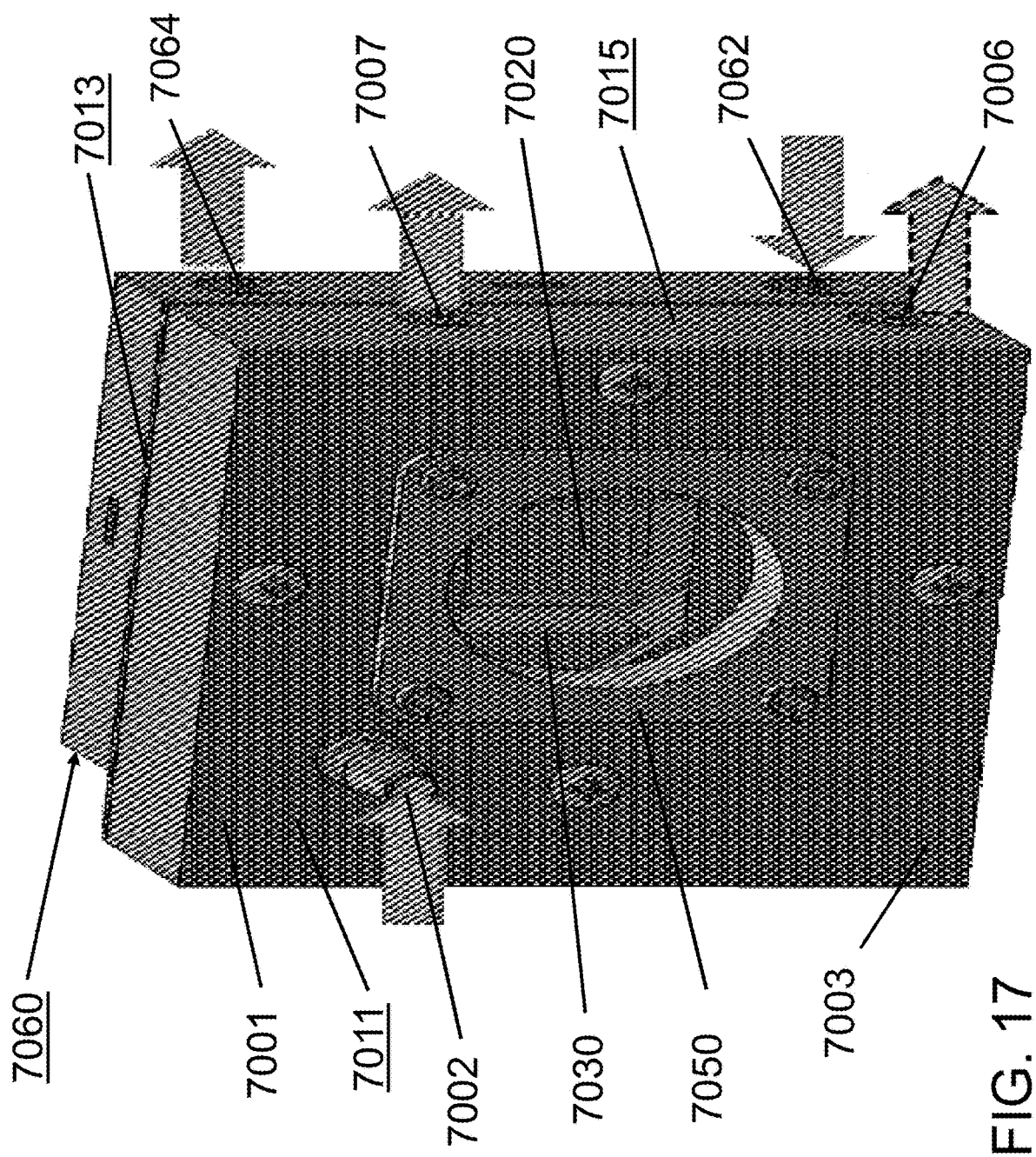
FIG. 17 is a perspective view of an example acoustophoretic device according to the present disclosure including a cooling unit for cooling the transducer.

During testing, it was also discovered that active cooling of the ultrasonic transducer led to greater throughput and efficiency and more power. As such, a cooling unit was developed for actively cooling the transducer, such as cooling unit 7060 coupled to the rear wall 7013 of acoustophoretic device 7000 depicted in FIG. 17. The cooling unit 7060 includes an independent flow path that is separate from the flow path through the device containing the fluid that is to be exposed to the multi-dimensional acoustic standing wave. A coolant inlet 7062 is adapted to permit the ingress of a cooling fluid into the cooling unit. A coolant outlet 7064 serves as the outlet through which the coolant and waste heat exit the cooling unit. Here, the coolant inlet is located below the coolant outlet, though this path can be varied as desired. The coolant that flows through the cooling unit can be any appropriate fluid. For example, the coolant can be water, air, alcohol, ethanol, ammonia, or some combination thereof. The coolant can, in certain embodiments, be a liquid, gas, or gel. The coolant can be an electrically non-conductive fluid to prevent electric short-circuits. The cooling unit can be used to cool the ultrasonic transducer, which can be particularly advantageously when the device is to be run continuously with repeated processing and recirculation for an extended period of time (e.g., perfusion). The cooling unit can also be used to cool the host fluid running through the device 7000, if desired.

Figure 18:
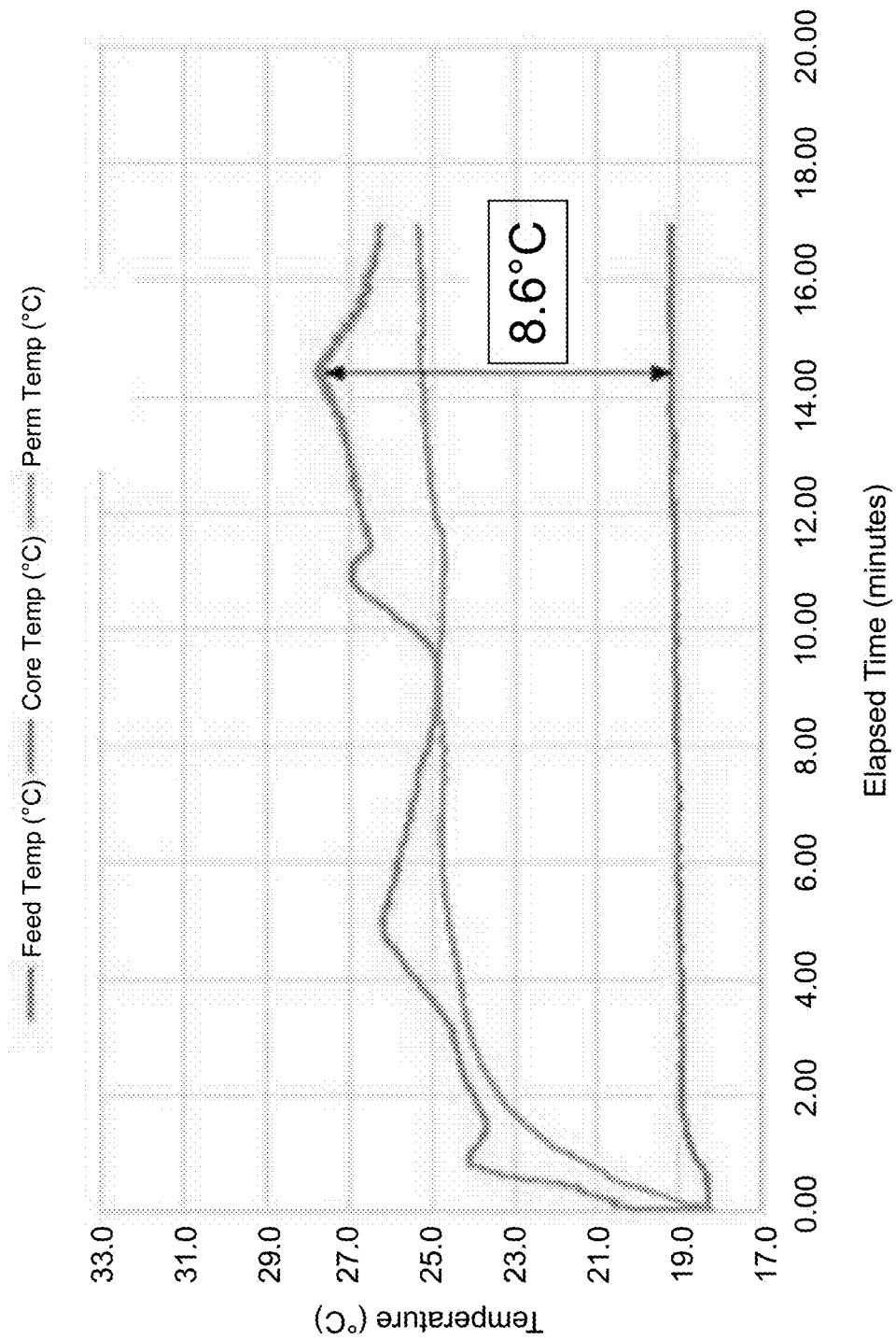
FIG. 18 is a graph showing the temperature profile of an acoustophoretic device without active cooling. The x-axis is elapsed time (minutes) and runs from 0.00 to 20.00 in increments of 2.00. The y-axis is temperature (° C.) and runs from 17.00 to 33.00 in increments of 2.00. The lowermost line along the right side of the graph represents the feed temperature (° C.). The uppermost line along the right side of the graph represents the core temperature (° C.). The middle line along the right side of the graph represents the permeate temperature (° C.).
Figure 19:
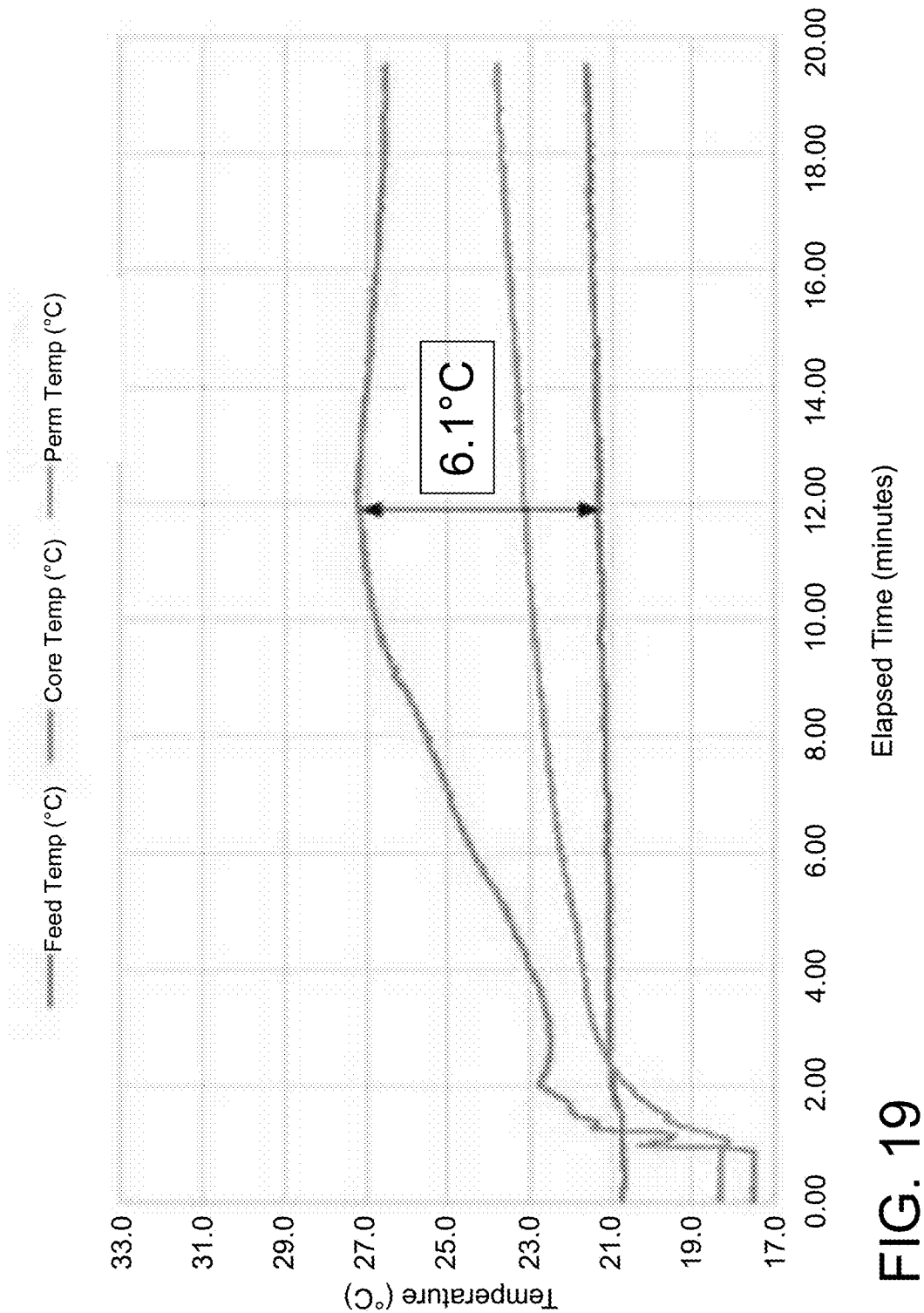
FIG. 19 is a graph showing the temperature profile of an acoustophoretic device with active cooling of the transducer. The x-axis is elapsed time (minutes) and runs from 0.00 to 20.00 in increments of 2.00. The y-axis is temperature (° C.) and runs from 17.00 to 33.00 in increments of 2.00. The lowermost line along the right side of the graph represents the feed temperature (° C.). The uppermost line along the right side of the graph represents the core temperature (° C.). The middle line along the right side of the graph represents the permeate temperature (° C.).

The advantages of providing a cooling unit for the transducer can be seen in FIG. 18 and FIG. 19. FIG. 18 graphically shows the temperature profile of the acoustophoretic device without any active cooling (e.g., without a cooling unit for the transducer). As seen in FIG. 18, the temperature difference between the feed and the core (e.g., the transducer) was 8.6° C. FIG. 19 graphically shows the temperature profile of the acoustophoretic device with active cooling (e.g., with a cooling unit for the transducer). As seen in FIG. 19, through the use of active cooling the temperature difference between the feed and the core was reduced to 6.1° C.

Figure 20:
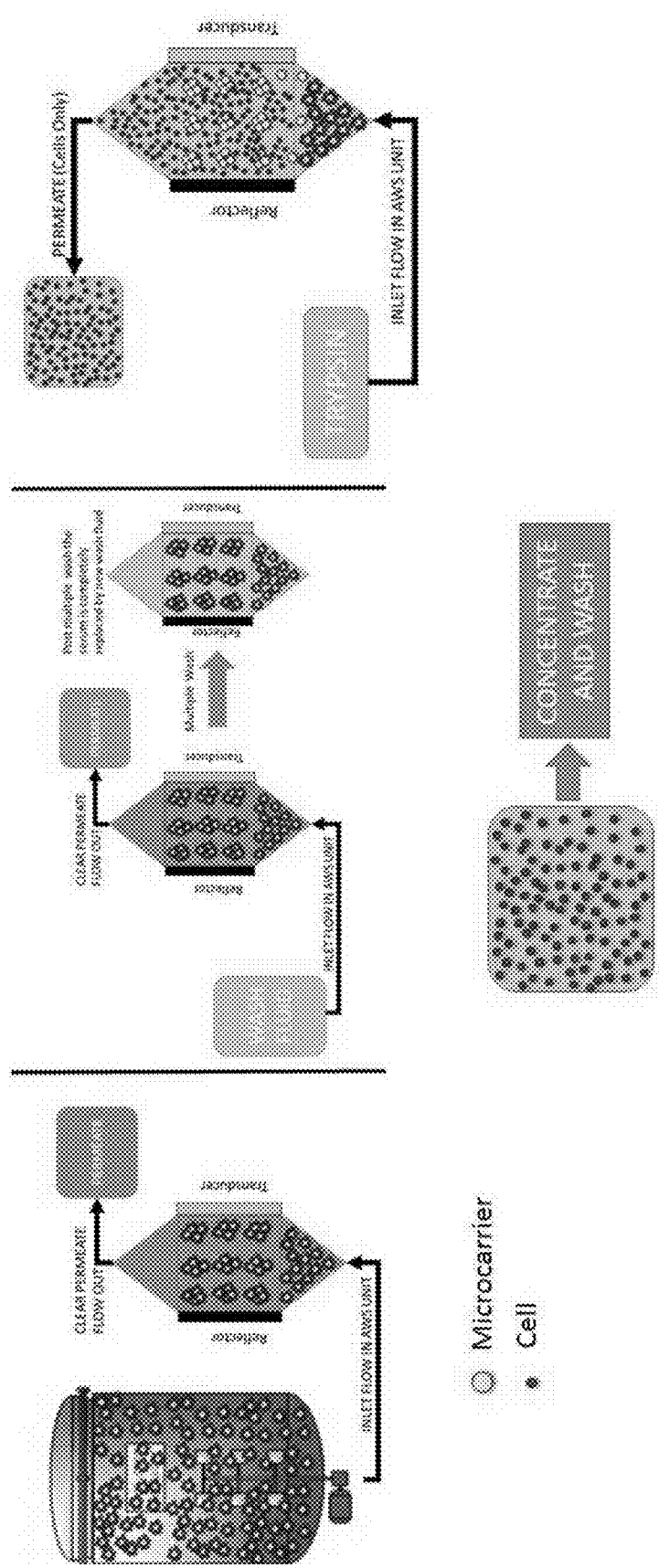
FIG. 20 illustrates a process for concentrating, washing, and/or separating microcarriers and cells according to the present disclosure. The leftmost portion represents a first step of receiving microcarriers and cells surrounded by a bioreactor serum from a bioreactor and concentrating the microcarriers with attached cells in an acoustophoretic device according to the present disclosure. The middle portion represents a second step of washing the concentrated microcarriers with attached cells to remove the bioreactor serum. The rightmost portion represents a third step of trypsinizing the microcarriers and separating the microcarriers from the cells in a fourth step. The bottom portion represents a final wash and concentrate step that can be employed as needed.

FIG. 20 illustrates a four-step process (with an optional fifth step) for concentrating, washing, and separating microcarriers from cells. The first step in the process involves concentrating the microcarriers with attached cells in an acoustophoretic device, such as those described herein. The microcarriers and attached cells can be introduced to the acoustophoretic device by receiving the microcarriers with attached cells from a bioreactor. In the bioreactor, the microcarriers and cells are suspended in a first media (e.g., growth serum or preservative material used to keep the cells viable in the bioreactor). The microcarriers with attached cells surrounded by the first media are concentrated by the acoustic standing wave(s) generated in the acoustophoretic device. In a second step, the concentrated microcarriers with attached cells are then washed with a second media to remove the first media (e.g., bioreactor growth serum or preservative material). The third step is to then introduce a third media containing an enzyme into the acoustophoretic device to detach the cells from the microcarriers through enzymatic action of the second media. In particular embodiments, trypsin is the enzyme used to enzymatically detach the cells from the microcarriers. The multi-dimensional acoustic standing wave can then be used to separate the cells from the microcarriers. Usually, this is done by trapping the microcarriers in the multi-dimensional acoustic standing wave, while the detached cells pass through with the third media. However, the cells can be trapped instead, if desired. Finally, the separated cells may optionally be concentrated and washed again, as desired.

After being concentrated and trapped/held in the multi-dimensional acoustic standing wave, the microcarriers can coalesce, clump, aggregate, agglomerate, and/or cluster to a critical size at which point the microcarriers fall out of the acoustic standing wave due to enhanced gravitational settling. The microcarriers can fall into a collector of the acoustophoretic device located below the acoustic standing wave, to be removed from the flow chamber.

Figure 21:
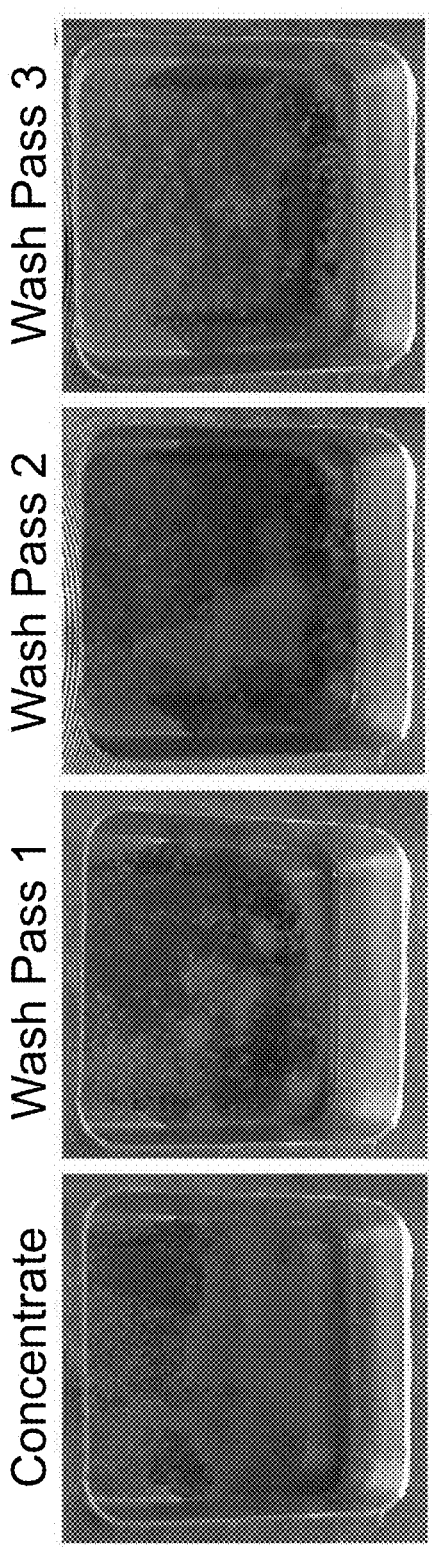
FIG. 21 shows media exchange in an acoustophoretic device according to the present disclosure. The "Concentrate" photograph shows the concentrate (e.g., concentrated microcarriers with attached T cells) surrounded by a first media (dyed red). The "Wash Pass 1" photograph shows the microcarriers with attached T cells after a first wash pass using a second media (dyed blue). The "Wash Pass 2" photograph shows the microcarriers with attached T cells after a second wash pass. The rightmost "Wash Pass 3" photograph shows the microcarriers with attached T cells after a third wash pass, and is almost completely blue.

During testing, steps one and two (i.e., concentration and washing) were performed using red and blue food dye to make colored fluid. The concentration mixture included SoloHill microcarriers in red fluid. The wash mixture included blue fluid and was passed through the device three times. The concentrate was observed under a microscope, as shown in the leftmost image of FIG. 21. The concentration step was shown to have a 99% efficiency. The remaining three images in FIG. 21 show microscopic images after the first, second, and third wash passes, respectively. As seen from left to right in FIG. 21, the first media (dyed red) is progressively washed out by a second media (dyed blue) over a series of wash passes. The light absorbance data is shown in the table below.

|  | Light Absorbance | |
| --- | --- | --- |
| Sample | Red (510 nm) | Blue (630 nm) |
| Feed | 0.138 | 0.041 |
| Wash Pass 1 | 0.080 | 0.066 |
| Wash Pass 2 | 0.063 | 0.080 |
| Wash Pass 3 | 0.054 | 0.084 |

The decrease in red light absorbance and increase in blue light absorbance evidences the feasibility of the washing steps.

Figure 22:
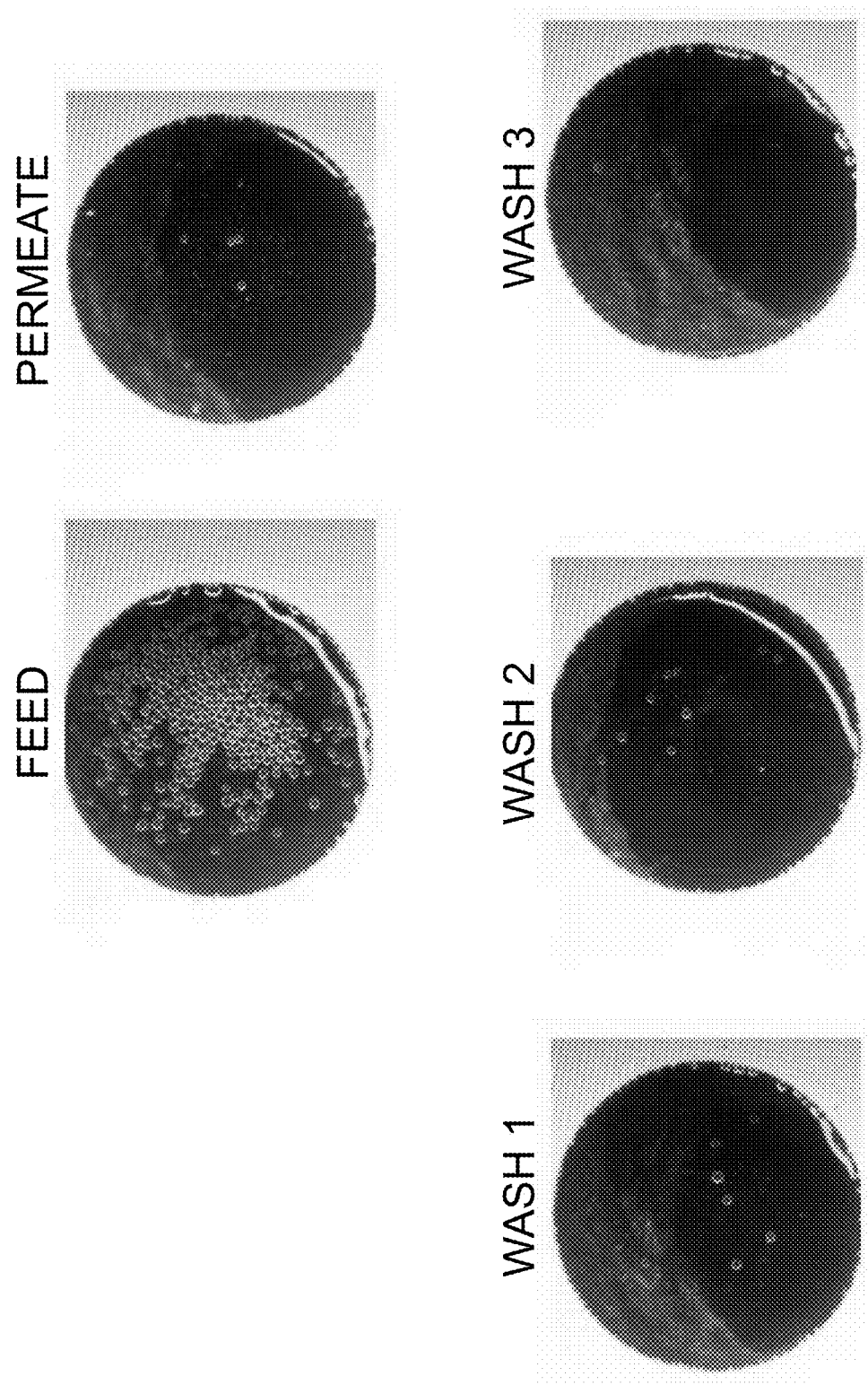
FIG. 22 shows microscopic images of the media exchange shown in FIG. 21.

FIG. 22 shows microscopic images of the microcarriers and attached cells during the concentration and washing steps. In particular, the leftmost image in the top row shows the microcarriers and attached cells in the feed, prior to introduction into the acoustophoretic device. The rightmost image in the top row shows the microcarriers and attached cells in the permeate, after concentration in the acoustophoretic device. The bottom row of images show the microcarriers and attached cells in the device during the washing step, namely during the first, second, and third wash passes, from left to right.

Figure 23:
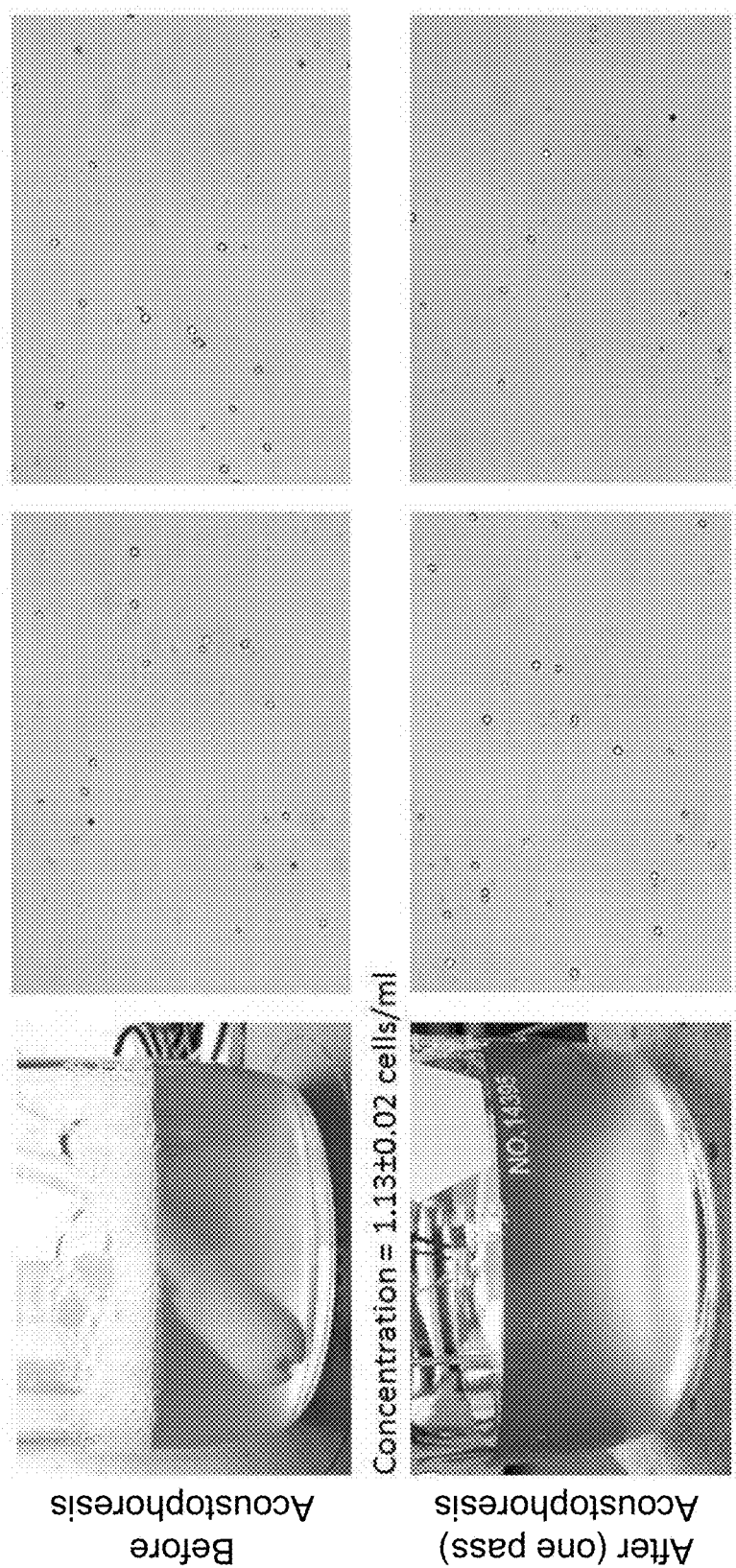
FIG. 23 shows the concentration of T cells in the acoustophoretic device before acoustophoresis (top row of photographs) and after one acoustophoresis pass (bottom row of photographs).

FIG. 23 shows the concentration of T-cells after being separated in the acoustophoretic device. The top row of images show the T-cells before acoustophoresis with a concentration of $1.14\pm0.03\times10^6$ cells/mL. The bottom row of images show the T-cells after acoustophoresis with a concentration of $1.13\pm0.02\times10^6$ cells/mL. The comparable concentrations evidence that substantially all of the cells pass through the acoustophoretic device, as the concentration was substantially unchanged by acoustophoresis.

Figure 24:
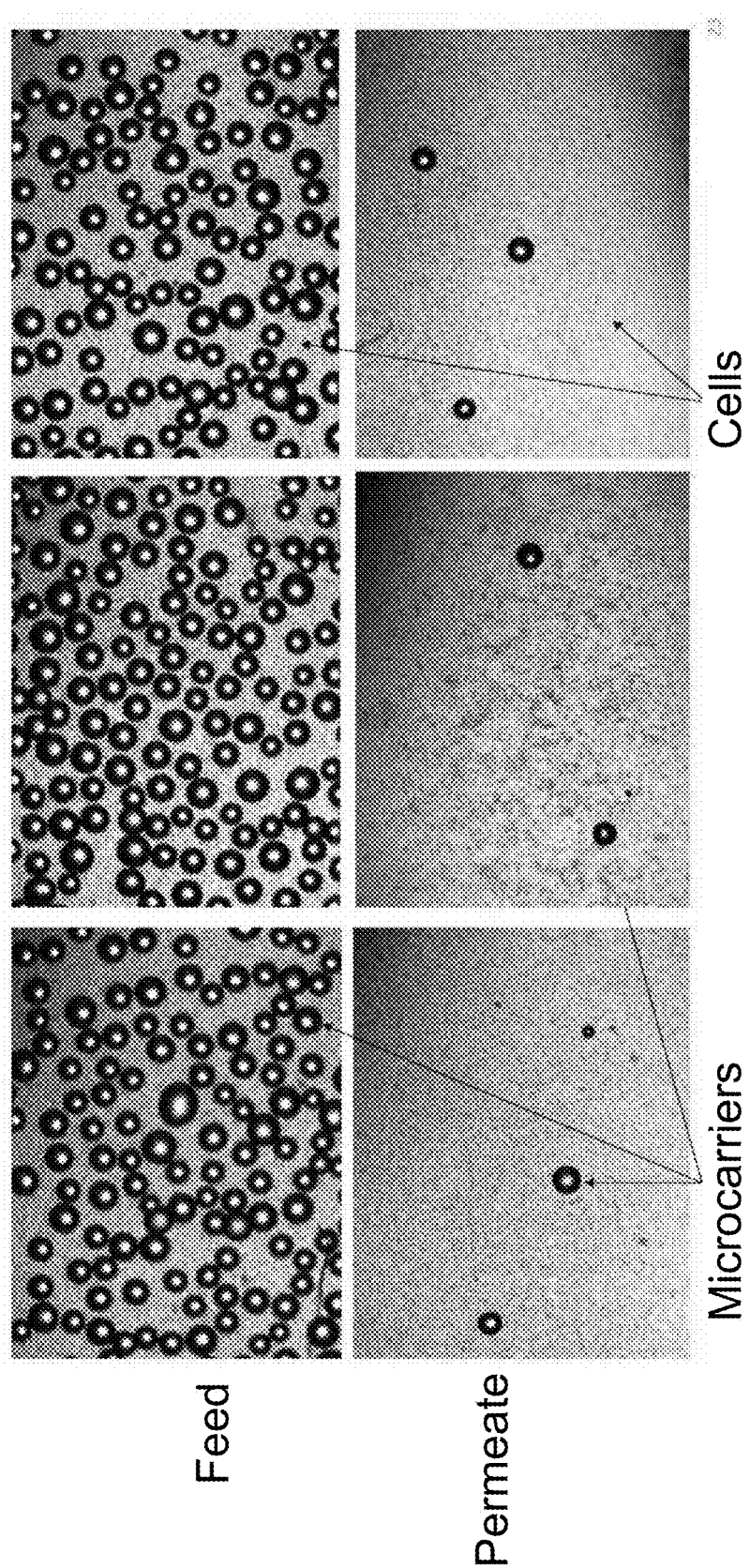
FIG. 24 shows the concentration of microcarriers with attached T cells in the feed into the acoustophoretic device (top row of photographs) and the concentration of separated microcarriers and T cells in the permeate drawn out of the acoustophoretic device (bottom row of photographs). The dark circular items indicate microcarriers, and the lighter area indicates T cells.
Figure 25:
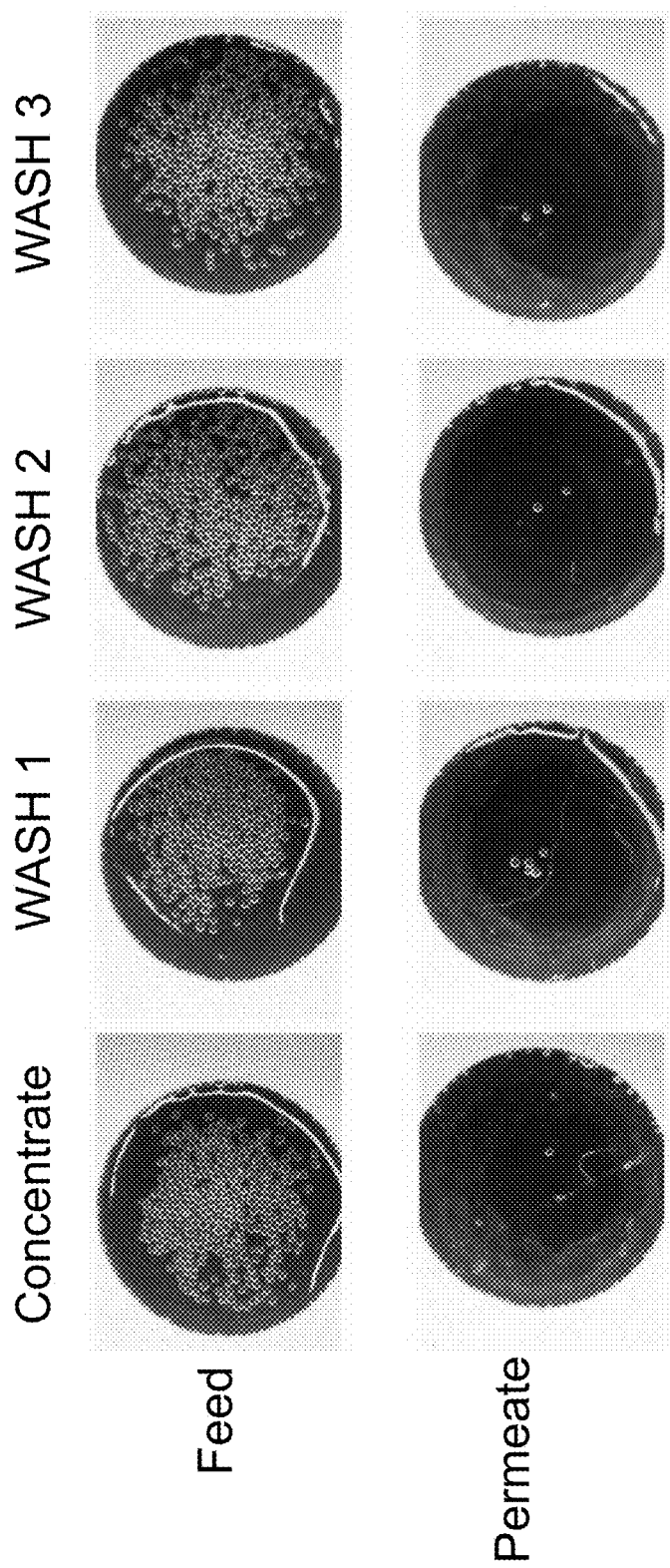
FIG. 25 shows microscopic images of the concentration of microcarriers with attached T cells in the feed and the concentration of separated microcarriers and T cells in the permeate.

FIG. 24 shows the presence of SoloHill microcarriers and T-Cells in the acoustophoretic device under 4× magnification. The top row of images show the microcarriers and cells in the feed before acoustophoresis. The bottom row of images show the microcarriers and cells in the permeate after the cells have been separated out by acoustophoresis. The difference in the number of microcarriers with the application of acoustophoresis evidences the feasibility of using the device for trapping the microcarriers in the device and separating the cells therefrom. The feasibility of this technique and the results are further evidenced by the images in FIG. 25, which show microscopic images of the microcarriers and cells in the feed (top row of images) and permeate (bottom row of images) after concentration and the first, second, and third washes, from left to right.

The testing of the acoustophoretic concentrating, washing, and separating process showed that the process is appropriate for cell therapy and microcarrier applications. The concentrate and wash steps were performed with a resulting efficiency of greater than 99%, and the separating step e.g., separating the cells from the microcarriers, was performed with greater than 98% efficiency.

Figure 26:
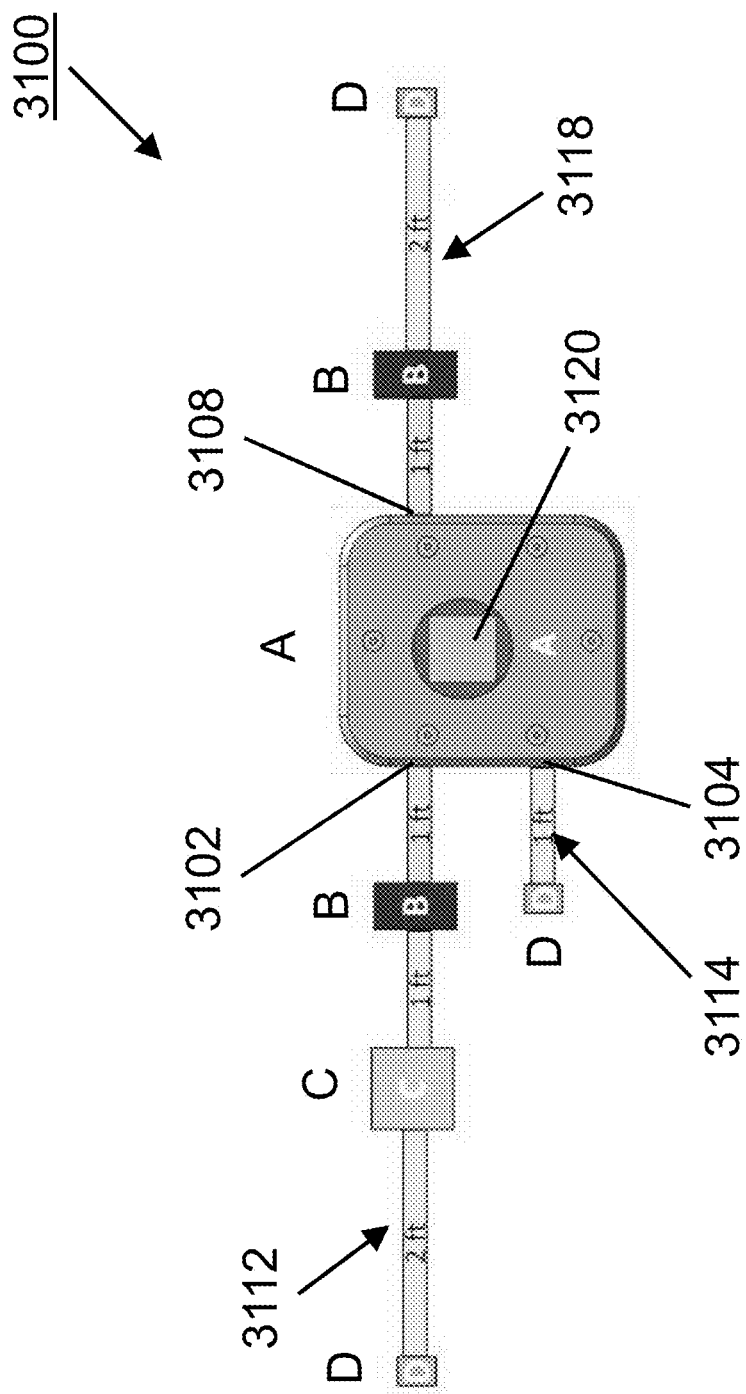
FIG. 26 is a schematic of an example acoustophoretic system according to the present disclosure.

FIG. 26 depicts an example embodiment of an acoustophoretic system/process 3100 employing an acoustophoretic device A, such as the acoustophoretic devices previously described. Generally, the device A includes a feed port 3102, a drain port 3104, a wash outlet 3108, and an ultrasonic transducer 3120 configured to create a multi-dimensional acoustic standing wave in the device, as explained in great detail herein.

The feed port 3102 of this example embodiment is generally configured to operate as an inlet to introduce a fluid into the device, with the fluid typically including material entrained therein, such as cells and/or microcarriers. As can be seen here, the feed port 3102 is connected to feed line 3112. In this example embodiment, feed line 3112 begins with a swabable barb valve D (Halkey Roberts) upstream of the feed port 3102. Also included in the feed line 3112 upstream of the feed port 3102 in this example embodiment are a disposable pump head C (NaoPump) and a temperature sensor B (SciLog SciTemp). The pump C can be used, for example, to regulate the flow rate of the acoustophoretic device so that gravity/buoyancy can act on cell clusters. The feed line 3112 generally terminates at the feed port 3102 of the device A.

The drain port 3104 of this example embodiment is generally configured to operate as a concentrate outlet for drawing off concentrate from the device A. As can be seen here, the drain port 3104 is connected to concentrate line 3114. In this example embodiment, concentrate line 3114 begins at the drain port 3104 of the device A and terminates with a swabable barb valve D (Halkey Roberts) downstream of the drain port 3104.

The wash outlet 3108 of this example embodiment is generally configured to remove material from the device A, such as separated cells and washed-out fluid and media. As can be seen here, the wash outlet 3108 is connected to wash line 3118. In this example embodiment, wash line 3118 begins at the wash outlet 3108 of the device A. Also included in the waste line 3118 downstream of the waste outlet 3108 in this example embodiment is a temperature sensor B (SciLog SciTemp) and a swabable barb valve D (Halkey Roberts).

The feed line 3112, concentrate line 3114, and waste line 3118 of this example embodiment are customarily made of tubing, preferably biopharmaceutical grade tubing (e.g., AdvantaHex Biopharmaceutical Grade TPE tubing having a 3.18 mm inner diameter and 6.35 mm outer diameter).

Figure 27:
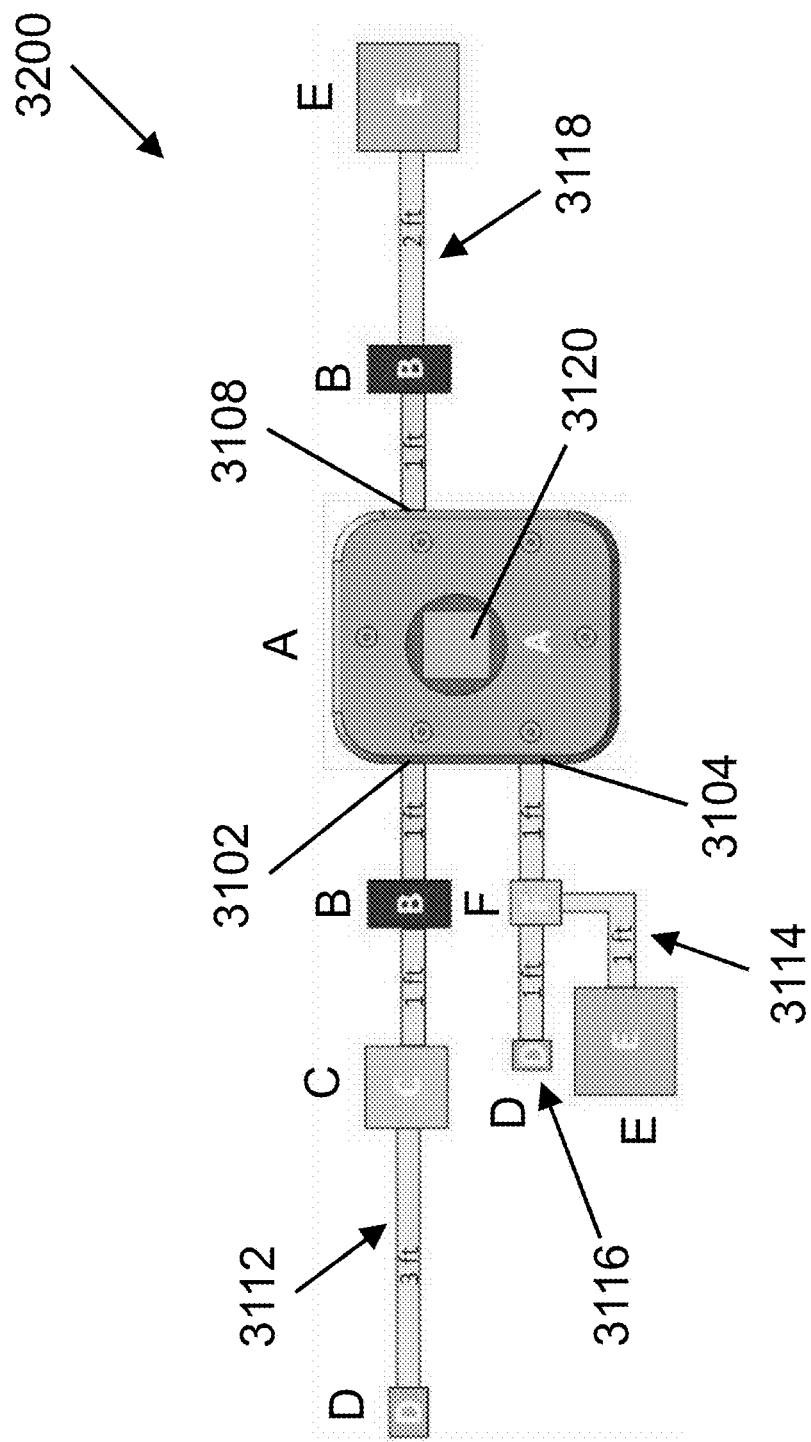
FIG. 27 is a schematic of another example acoustophoretic system according to the present disclosure including waste and concentrate transfer bags.

Turning now to FIG. 27, another example embodiment of an acoustophoretic system/process 3200 is depicted. The acoustophoretic device 3200 of FIG. 27 is very similar to the acoustophoretic system/process 3100 of FIG. 26. However, the acoustophoretic system/process 3200 depicted in FIG. 32 includes a drain port 3104 configured to operate as both a wash inlet and a concentrate outlet. In this way, the drain port 3104 is used to introduce a wash media/buffer into the device A and to draw off concentrate from the device A. Because of the dual purpose of the drain port 3104, as can be seen here, the drain port 3104 is connected to both a concentrate line 3114 and a wash line 3116. The concentrate line 3114 and the wash line 3116 are joined together upstream of the drain port 3104 by a valve/stopcock F. As can be seen here, wash line 3116 of this example embodiment begins at swabable barb valve D (Halkey Roberts), runs through the stopcock F (Halkey Roberts), and terminates at the drain port 3104. The concentrate line 3114, on the other hand, begins at the drain port 3104, runs through the stopcock F, and terminates at a collection container E (Charter Medical transfer bag, 400 mL). In this way, the concentrate line 3114 and the wash line 3116 share the valve/stopcock F, where the two lines are joined and share a common tubing between the stopcock F and the drain port 3104. Additionally, this acoustophoretic system/process 3200 differs from the acoustophoretic system/process 3100 depicted in FIG. 31 by the replacement of the barb valve at the end of the waste line 1318 in system 3100 with a collection container E (Charter Medical transfer bag, 400 mL) in system 3200. The feed line 3112, concentrate line 3114, wash line 3116, and waste line 3118 are customarily made of tubing, preferably biopharmaceutical grade tubing (e.g., Escelero RNT Clean Flexible PVC tubing tubing having a 3.18 mm inner diameter and 4.76 mm outer diameter).

The use of collection containers E at the ends of the concentrate and waste lines advantageously creates an enclosed primary environment within which concentration, washing, and/or separation of cells and cellular materials can occur, which helps to prevent the cells/cell culture/cellular material from being exposed to possible intrusions, pathogens, or outside cellular influences that would be harmful.

Figure 28:
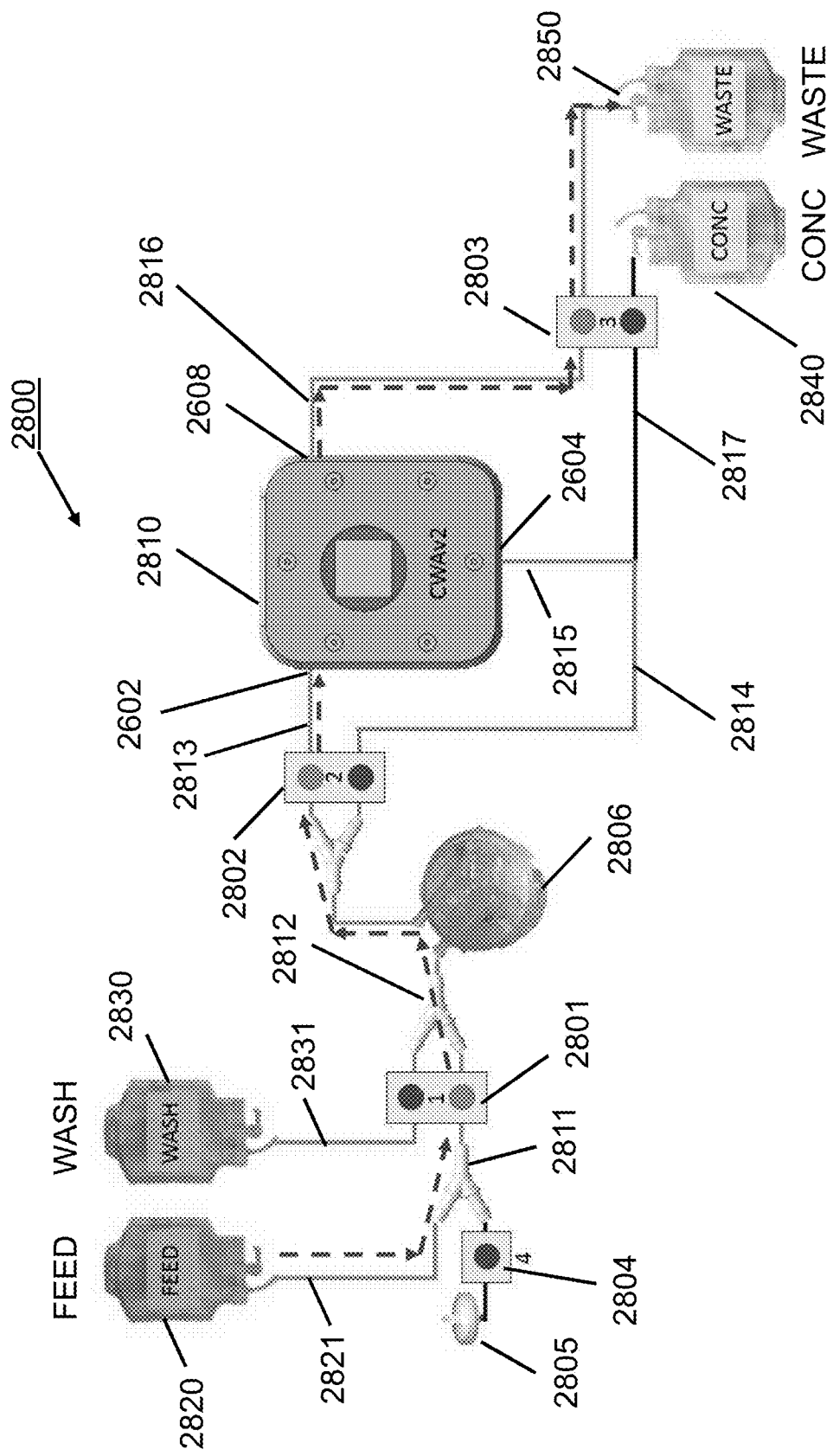
FIG. 28 is a schematic of an example acoustophoretic system according to the present disclosure showing the flow path of the feed material through the system.
Figure 29:
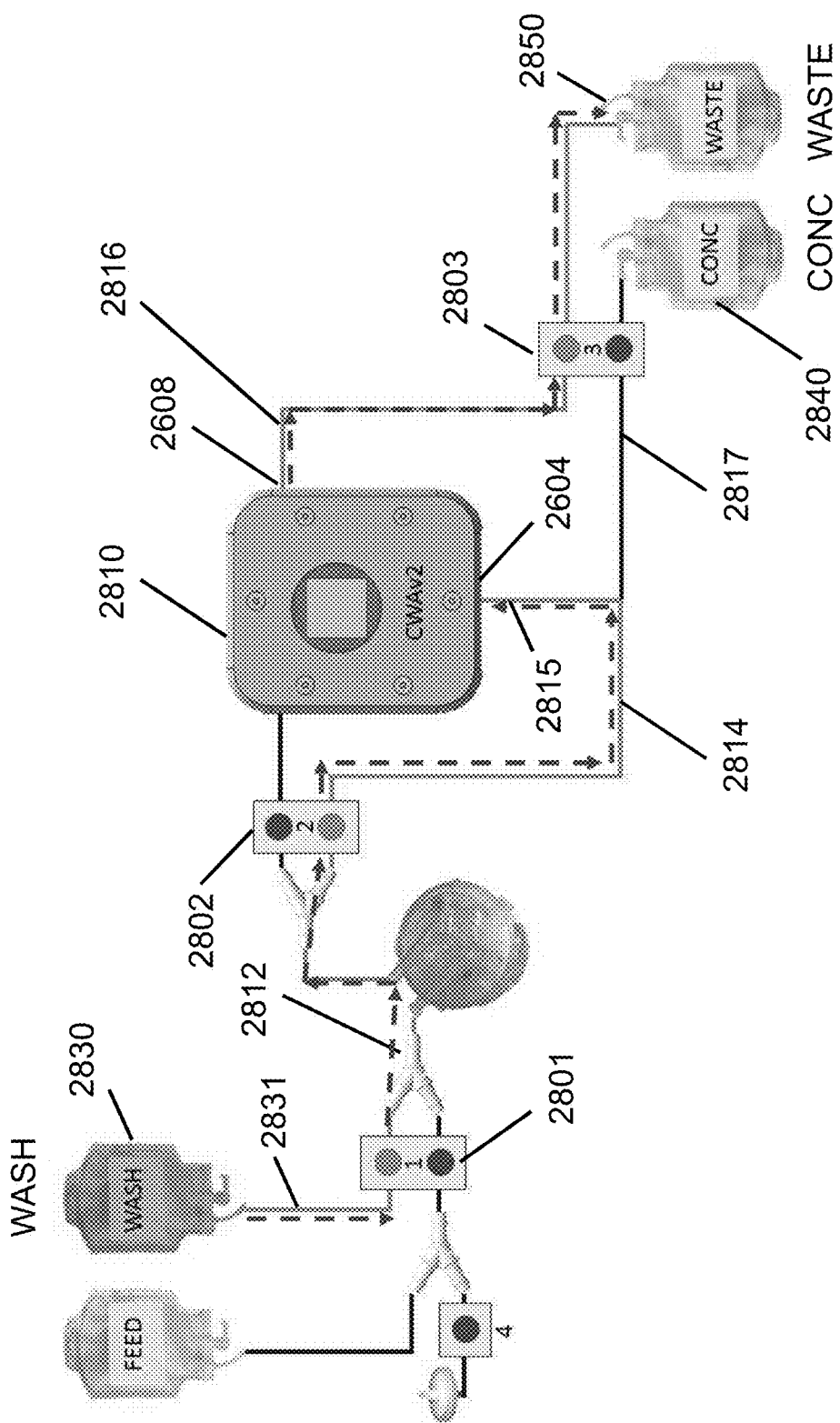
FIG. 29 is a schematic of the example acoustophoretic system of FIG. 28 showing the flow path of the wash material through the system.
Figure 30:
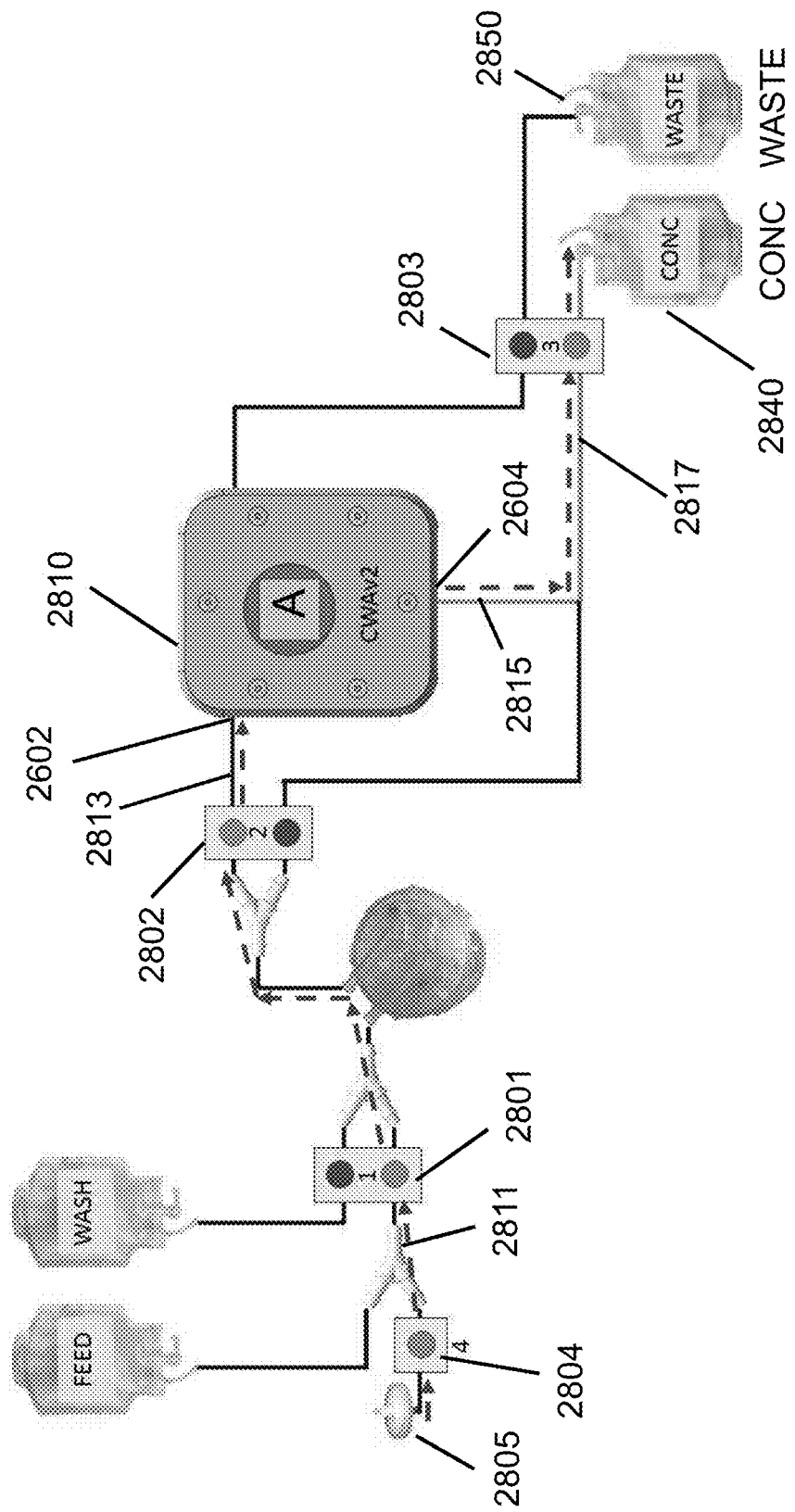
FIG. 30 is a schematic of the example acoustophoretic system of FIG. 28 showing draining of the system.

FIGS. 28-30 illustrate another example embodiment of an acoustophoretic system/process 2800 including a disposable acoustophoretic device 2810 with solenoid pinch valves that control the flow of fluid therethrough. Starting from the left-hand side of FIG. 28, the system includes a feed tank 2820, a wash tank 2830, and an air intake 2805. The air intake 2805 runs through an air intake valve 2804. Feed line 2821 runs from the feed tank 2820. The air intake and the feed line 2821 are joined together by a Y-connector into common feed line 2811, which runs into feed selector valve 2801. A wash line 2831 runs from the wash tank 2830, and also runs into feed selector valve 2801. Feed selector valve 2801 permits only one line to be open at a given time (valves 2802, 2803 also operate in this manner). Wash line 2831 and feed line 2811 are joined together by a Y-connector downstream of the feed selector valve 2801 into input line 2812. Input line 2812 passes through pump 2806 to inflow selector valve 2802, which is downstream of the feed selector valve 2801 and upstream of the acoustophoretic device 2810. The inflow selector valve 2802 selectively controls the inflow of feed or wash into the acoustophoretic device 2810 through either feed port 2602 or wash/drain port 2604. A feed line 2813 runs from the inflow selector valve 2802 to feed port 2602. A wash line 2814 runs from the inflow selector valve 2802 to common line 2815 and into wash/drain port 2604.

On the right-hand side of FIG. 28, an outflow selector valve 2803 is located downstream of the acoustophoretic device 2810 and controls the outflow of fluid therefrom. A waste line 2816 runs from waste port 2608 through outflow selector valve 2803 and subsequently to waste tank 2850. The common line 2815 runs into drain line 2817, which then passes through outflow selector valve 2803 and subsequently to concentrate tank 2840. These tanks 2840, 2850 can be, for example, bags such as the culture bag that will be described further herein in FIG. 31. The outflow selector 2803 thereby selectively controls the flow of fluid to the concentrate tank and waste tank.

FIG. 28 also illustrates the flow path of the feed material through the system. In this example embodiment, feed selector valve 2801 is operated with the bottom open (and top closed), so that the feed from feed tank 2820 flows through. Inflow selector valve 2802 is operated with the top open (and bottom closed), so that the feed material enters the acoustophoretic device 2810 via feed port 2602. The outflow selector valve 2803 is also operated with the top open (and bottom closed) so that the fluid/first media of the feed material flows through to waste tank 2850. The targeted particles in the feed material (e.g., microcarriers or cells) are trapped in the acoustophoretic device 2810 by action of a multi-dimensional acoustic standing wave(s), as explained in detail herein.

FIG. 29 illustrates the flow path of the wash material through the system. Feed selector valve 2801 is operated with the top open (and bottom closed), so that the wash material from wash tank 2830 flows through. The inflow selector valve 2802 is operated with the bottom open (and top closed) and the outflow selector valve 2803 is operated with the top open (and bottom closed). As a result, the wash material enters the acoustophoretic device 2810 via wash/drain port 2604, which operates as a wash inlet. Note that the closed outflow selector valve 2803 prevents the wash material from entering concentrate tank 2840. The wash material can then pass through the acoustophoretic device 2810 and remove the first media (e.g., bioreactor serum or preservative material). The wash material then exits via waste port 2608, and flows to waste tank 2850. The target particles remain trapped in the acoustophoretic device 2810.

FIG. 30 illustrates the draining of the system (e.g., the collection of the target particles). Air intake valve 2804 is opened. The feed selector valve 2801 is operated with the bottom open (and top closed), and the inflow selector valve 2802 is operated with the top open (and bottom closed), so that air enters the acoustophoretic device 2810 via feed port 2602. The air generally aids in dislodging the clusters of target particles from the acoustophoretic device 2810. The outflow selector valve 2803 is operated with the bottom open (and top closed). The target particles flow out of wash/drain port 2604 through common line 2815, through drain line 2817 and subsequently to concentrate tank 2840.

Figure 31:
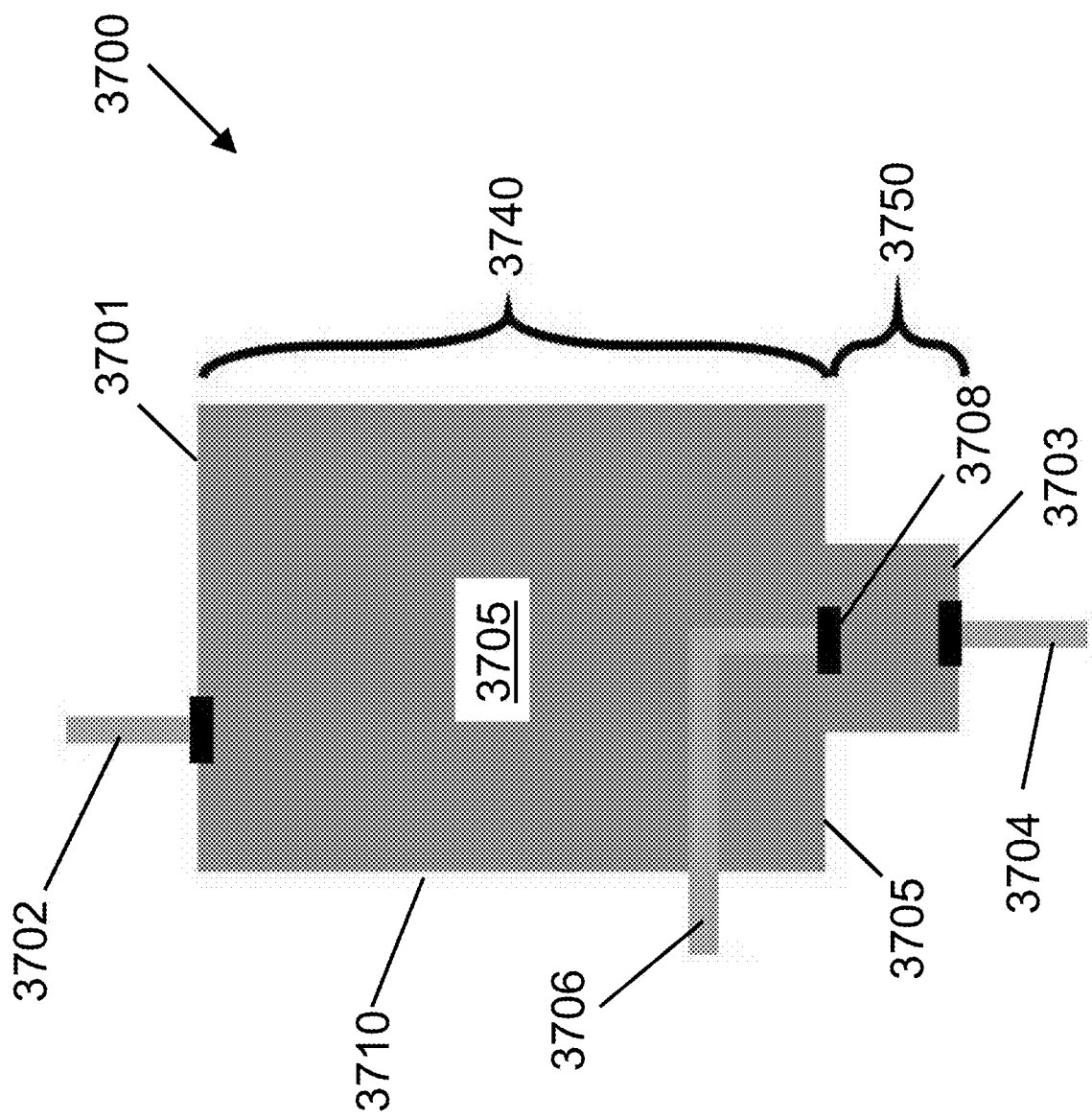
FIG. 31 illustrates a culture bag for use in the acoustophoretic systems according to the present disclosure.

FIG. 31 depicts an example embodiment of a culture bag 3700 that can be used in the acoustophoretic device 2810 of FIG. 28. The culture bag is formed from a sidewall 3710 that surrounds an internal volume 3705. The bag 3700 can be thought of as having an upper portion 3740 and a lower portion 3750. The culture bag 3700 includes a fill port 3702 at an upper end 3701 thereof, and a drain port 3704 at a lower end 3703 of the bag 3700. The upper end 3701 and lower end 3703 of the bag 3700 are located opposite one another.

The bag 3700 further includes a wash outlet 3706 at a bottom end 3705 of the upper portion 3740. As seen here, the wash outlet 3706 is generally located above the drain port 3704 of the bag 3700. A pipe connects the wash outlet 3706 to a wash inlet 3708 that is located in the lower portion 3750 of the bag.

The upper portion 3740 of the bag includes the fill port 3702 and the wash outlet 3708. The lower portion 3750 includes the wash inlet 3708 and the drain port 3704. In particular illustrative embodiments, the upper portion 3740 can have a volume of about 880 mL and the lower portion 3740 can have a volume of about 20 mL, although it is to be understood that the size and volume of the bag 3700 can be varied as desired and/or in accordance with a particular application. In particular embodiments, the lower portion comprises from about 1% to about 5% of the internal volume, with the upper portion comprising from about 95% to about 99% of the internal volume.

The bag 3700 is generally formed from a substantially acoustically transparent material, such as a polymeric material. For example, the bag may be made from at least one polymer layer (e.g., polyethylene, polypropylene, polyethylene terephthalate (PET), polymethylpentene and the like). The bag can be a multilayer bag (e.g., made from multiple layers of differentially functioning polymer layers). Those polymer layers may function as a waterproof layer, as a layer that provides strength, etc. For example, in some instances, the exterior (i.e. outermost layer) of the bag is a polyethylene terephthalate (PET) polymer. A middle or central layer of the bag can be typically ethylene vinyl alcohol (EVOH) or polyvinyl acetate (PVA). The interior layer can be typically a polyethylene polypropylene such as low-density polyethylene or very low density polyethylene. The bag has a large interior volume, generally of at least one liter, up to 1000 liters, and even larger as desired. The bag 3700 may be formed from any material suitable for allowing the passage of the acoustic standing wave(s) generated by the transducer (s) of the present disclosure therethrough.

The culture bag 3700 can be used in the acoustophoretic device 2810 of FIG. 28, or can be used in the concentrate tank 2840 or the waste tank 2850. If used in the concentrate tank, the culture bag 3700 can be further processed to concentrate the target particles even more. This additional processing is illustrated in a system as shown in FIG. 32.

Figure 32:
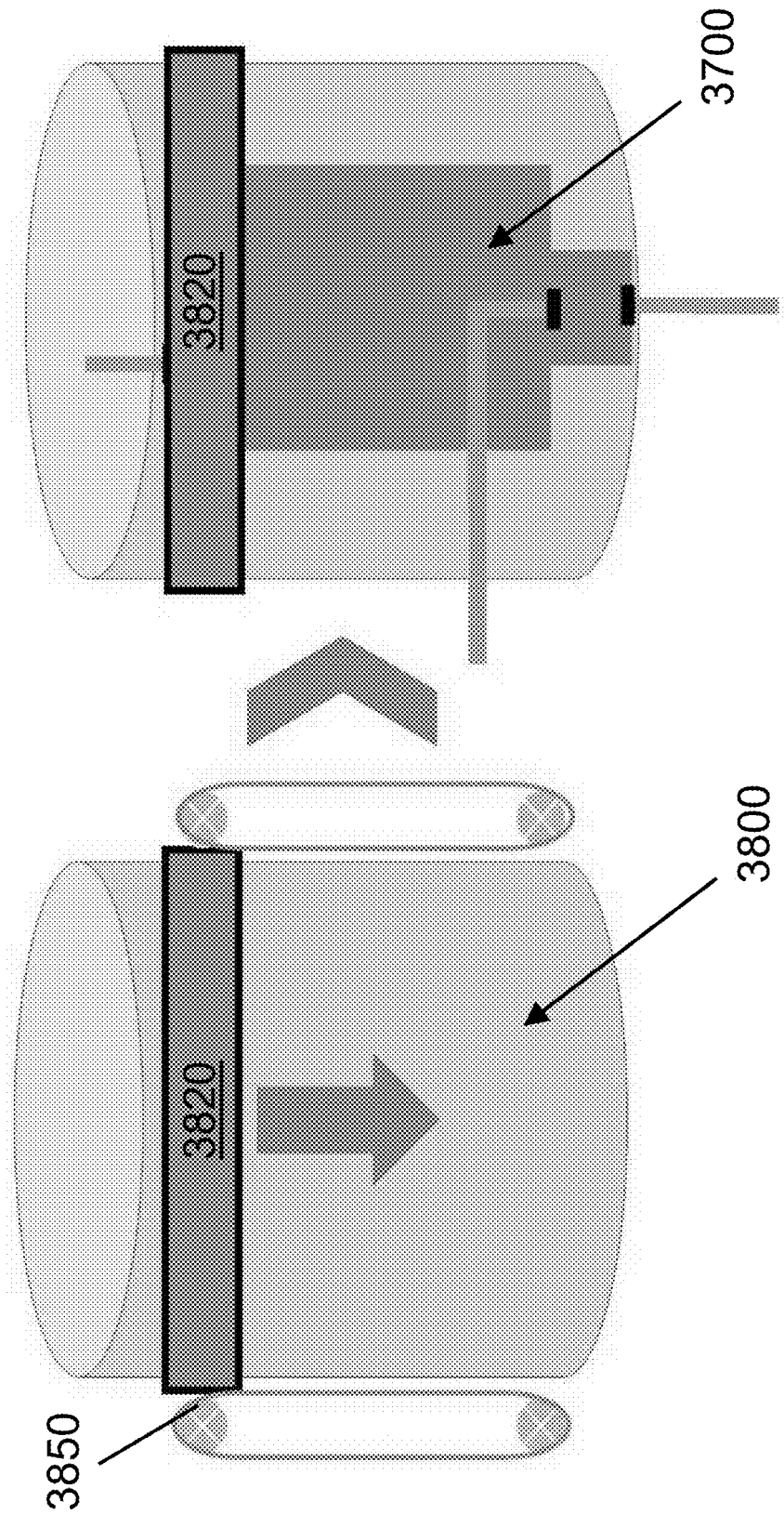
FIG. 32 illustrates the concentrate transfer bag of FIG. 31 disposed within a tank filled with fluid and a conveyor system for moving the transducer relative to the bag.

As seen in the left-side image of FIG. 32, the system includes a container 3800 that is filled with a fluid, such as water. An ultrasonic transducer 3820 is also provided. Generally, means for moving the transducer 3820 (along with a reflector, when desired) relative to the interior of the container are provided. For example, the transducer 3820 is cooperatively attached to a conveyor system 3850 that is configured to move the transducer 3820 vertically relative to the container 3800 and as indicated by the arrow. The transducer can produce a multi-dimensional acoustic standing wave as previously described.

The right-side image of FIG. 32 shows the culture bag 3700 in use disposed within the container 3800. Generally, the movement of the transducer relative to the bag creates a "sweeping effect" through the media and particles in the bag 3700 from the upper end 3701 to the lower end 3703 (i.e., from the upper portion 3740 to the lower portion 3750 of the bag 3700) or vice versa, depending on the direction of the vertical movement. This "sweeping" of the media in the bag improves the settling or buoyancy of particulate material (e.g., cells, cellular material) that is disposed within the media. While a conveyor system is depicted here for movement of the transducer relative to the container and the bag, it is to be understood that other suitable structures can be used to achieve the same means.

Figure 33:
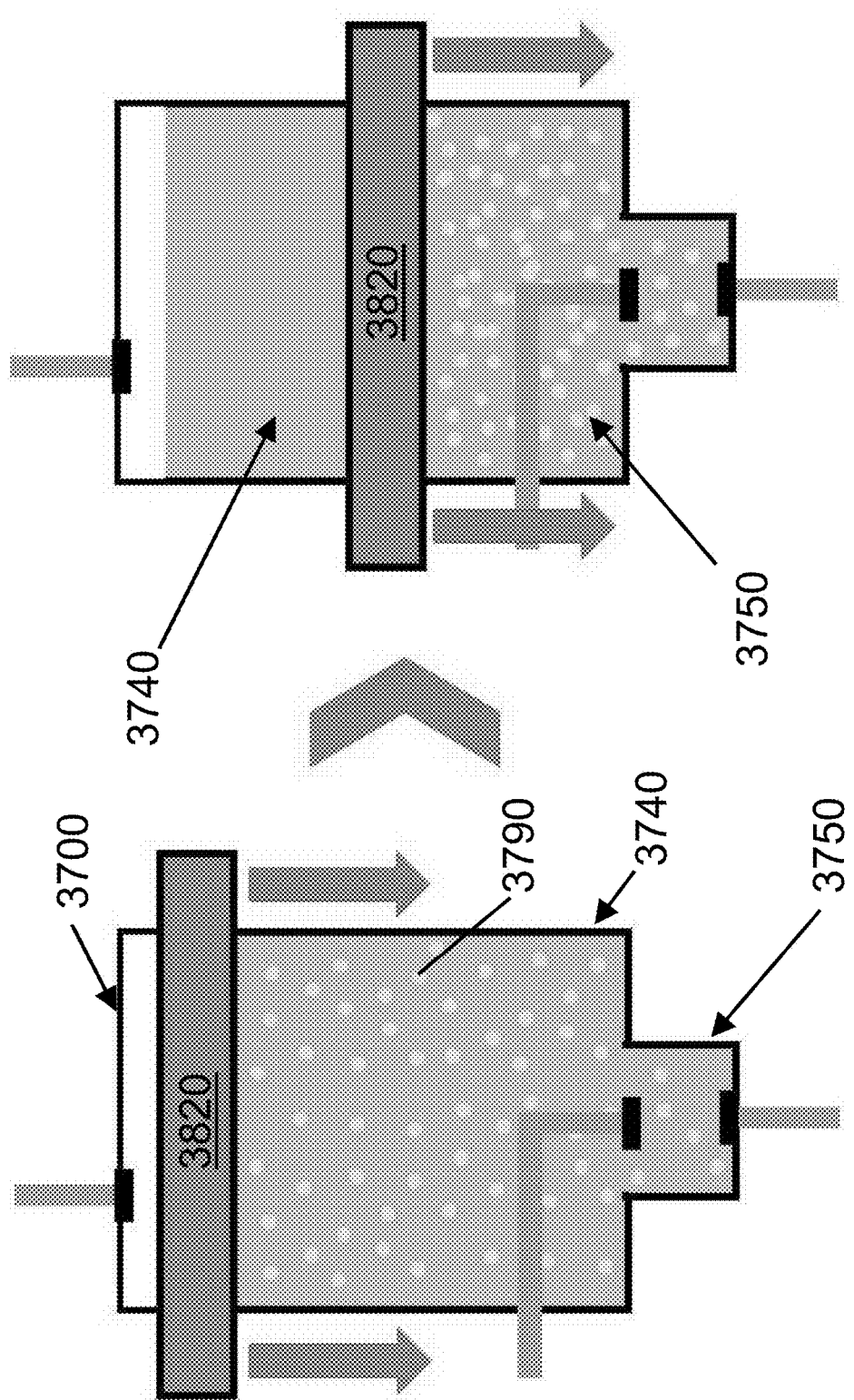
FIG. 33 illustrates moving the transducer from an upper portion of the bag to a lower portion of the bag to concentrate cellular material in the lower portion of the bag.

FIG. 33 illustrates the process of causing material in the bag 3700 to settle into the lower portion 3750. As seen on the left-hand side, the ultrasonic transducer 3820 begins at the top of the container, and moves downwards towards the lower portion 3750. The ultrasonic transducer 3820 generates an acoustic standing wave that causes the particles 3790 to settle out. As seen in the right-hand side, the movement of the ultrasonic transducer 3820 while generating an acoustic standing wave results in the upper portion 3740 containing media with a reduced concentration of particles, and the lower portion 3750 containing media with an increased concentration of particles.

Figure 34:
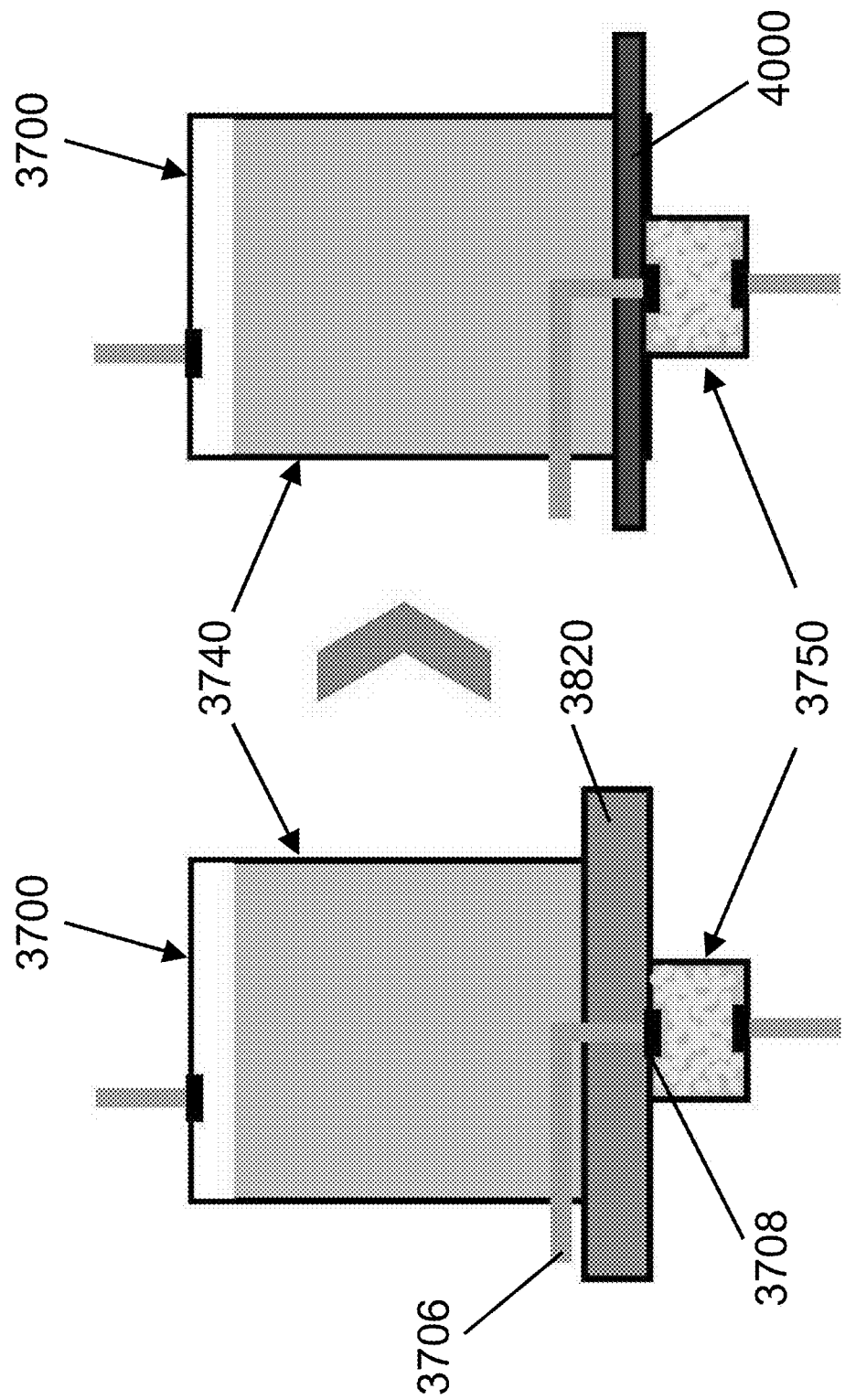
FIG. 34 illustrates concentrating the cellular material in the lower portion of the bag and sealing the bag between the upper and lower portions.

Referring now to the left-hand side of FIG. 34, the ultrasonic transducer 3820 has ended its cycle, and the particles are present in the lower portion 3750. As seen on the right-hand side of FIG. 34, means 4000 may be provided in the system for sealing the culture bag between the upper portion 3740 and the lower portion 3750. For example, in one embodiment, the means 4000 may be a heating bar that pinches the two sides of the culture bag together and heats the bag so as to form a seal between the upper portion and the lower portion. In other embodiments, the means 4000 can be a radio frequency (RF) sealer or an ultrasonic sealer.

Figure 35:
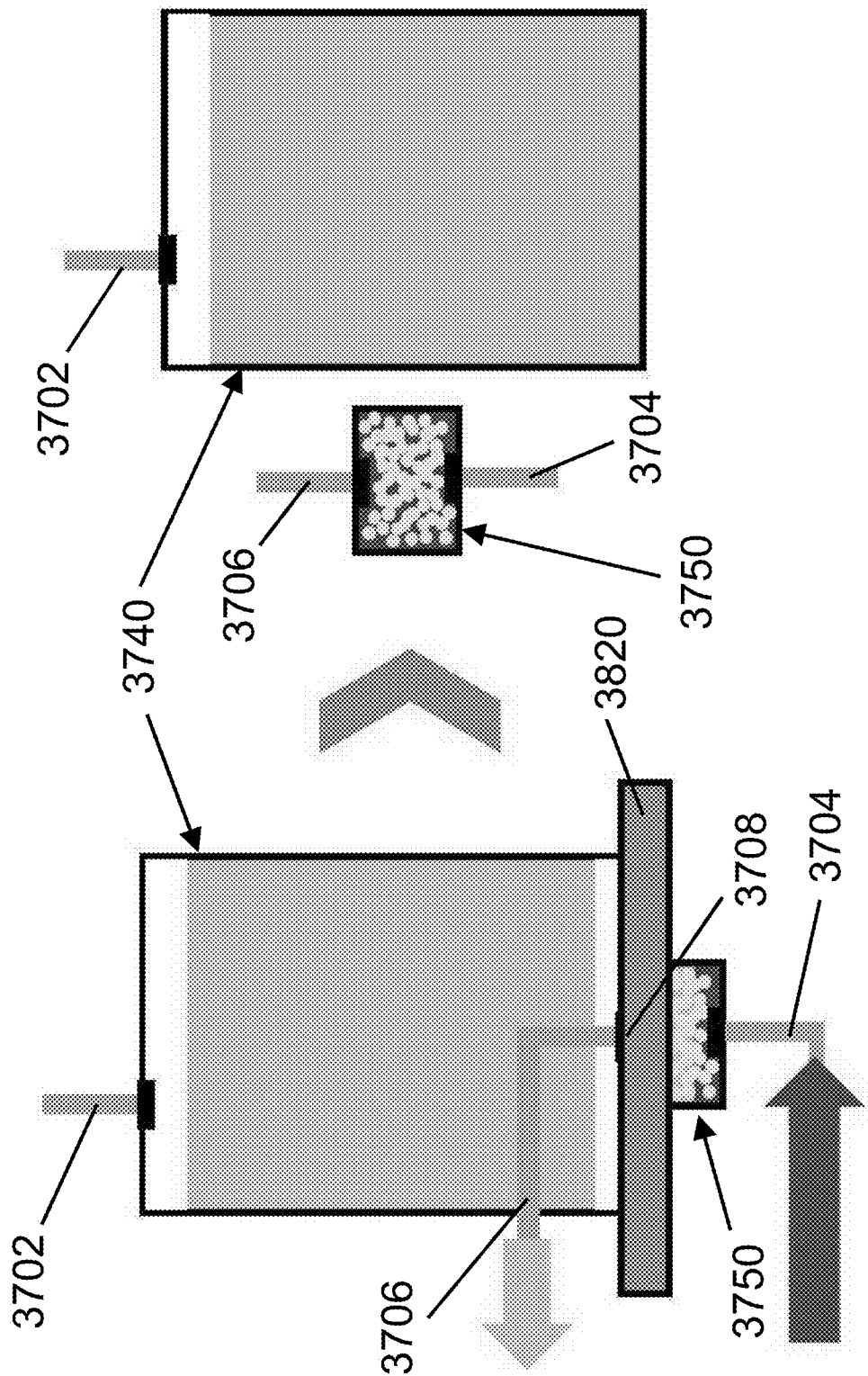
FIG. 35 illustrates removing the waste from the lower portion of the bag via the waste outlet, introducing a new wash buffer via the drain port, and then separating the lower portion of the bag containing the concentrated cellular material from the upper portion of the bag.

Turning now to FIG. 35, it should be noted that the waste inlet 3708 is still part of the now-sealed lower portion 3750. As illustrated here, a wash fluid or buffer can be introduced into the lower portion 3750 of the bag 3700 via the wash/drain port 3704. This wash fluid or buffer displaces the media that was originally present in the lower portion 3750. The original media exits via wash inlet 3708 and wash outlet 3706. Thus, in certain embodiments, the wash/drain port 3704 can serve the dual function of acting as both a concentrate outlet and a wash inlet, as previously explained. After washing the material in the lower portion 3750 of the bag 3700, the upper and lower portions of the bag can be separated from one another as illustrated on the right-hand side of FIG. 35. The upper portion 3740 generally contains residual media, while the lower portion 3750 contains the target particles, which can be removed. After removal, the target particles (e.g. therapeutic cells) in the lower portion can be further processed and prepared for use with a patient.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method of washing particles, the method comprising:
providing an initial mixture of a first media and particles to a chamber of an acoustophoretic device, the acoustophoretic device also comprising at least one ultrasonic transducer that includes a piezoelectric material;
driving the at least one ultrasonic transducer to create an acoustic standing wave in the chamber, such that at least a portion of the particles are trapped and held against fluid flow in the acoustic standing wave;
forming clusters of the trapped particles to grow in size to exit the acoustic standing wave; and
mixing the trapped particles and clusters with a second media to wash the trapped particles and clusters.

2. The method of claim 1, further comprising:
providing the initial mixture to the chamber to obtain an intermediate mixture of the trapped particles in a reduced volume of the first media;
collecting the intermediate mixture;
mixing the intermediate mixture with the second media to form a secondary mixture; and
providing the secondary mixture to the chamber to obtain a final mixture of the trapped particles in a reduced volume of the second media.

3. The method of claim 1, wherein the second media is provided to the chamber after the initial mixture is provided to the chamber.

4. The method of claim 1, wherein the acoustophoretic device further comprises a collector for collecting the trapped particles and clustered particles therein, the collector located below the at least one ultrasonic transducer; and
wherein the collector leads to a collection container that contains the second media.

5. The method of claim 1, wherein the second media is a biocompatible wash or a buffer solution.

6. The method of claim 1, wherein the particles are cells.

7. The method of claim 6, wherein the cells are Chinese hamster ovary (CHO) cells, NS0 hybridoma cells, baby hamster kidney (BHK) cells, human cells, regulatory T-cells, Jurkat T-cells, CAR-T cells, B cells, or NK cells, peripheral blood mononuclear cells (PBMCs), algae, plant cells, bacteria, or viruses.

8. The method of claim 6, wherein the cells are attached to microcarriers.

9. The method of claim 1, wherein the piezoelectric material of the at least one ultrasonic transducer is in the form of a piezoelectric array formed from a plurality of piezoelectric elements.

10. The method of claim 9, wherein the piezoelectric elements are operated out of phase with each other.

11. The method of claim 1, wherein the acoustophoretic device further comprises a cooling unit for cooling the at least one ultrasonic transducer.

12. The method of claim 1, wherein the acoustic standing wave is a multi-dimensional acoustic standing wave.

13. The method of claim 1, wherein, over time, the second media gradually displaces the first media in the flow chamber of the acoustophoretic device.

14. A method of separating microcarriers from cells, comprising:
feeding an initial mixture of a first media and microcarriers with attached cells thereon through a flow chamber of an acoustophoretic device, the acoustophoretic device comprising at least one ultrasonic transducer including a piezoelectric material that is configured to be driven to create an acoustic standing wave in the flow chamber;
driving the at least one ultrasonic transducer to create an acoustic standing wave in the flow chamber, and to trap and hold against fluid flow at least a portion of the microcarriers with attached cells in the acoustic standing wave;
forming clusters of the at least portion of the microcarriers with attached cells in the acoustic standing wave to grow in size to exit the acoustic standing wave;
washing the trapped microcarriers with attached cells and clusters by flowing a second media through the flow chamber to remove the first media; and
flowing a third media containing an enzyme through the flow chamber to separate the cells from the microcarriers.

15. The method of claim 14, wherein the microcarriers remain trapped in the acoustic standing wave or clusters, and further comprising recovering a mixture of the cells and the third media.

16. The method of claim 14, wherein the enzyme is trypsin.

17. A culture bag, comprising:
a sidewall that surrounds an internal volume, the internal volume including an upper portion and a lower portion;
a fill port at an upper end of the culture bag in the upper portion;
a drain port at a lower end of the culture bag in the lower portion; and
a wash outlet located at a bottom end of the upper portion between the fill port and the drain port;
wherein the upper portion has a larger diameter than the lower portion.

18. The culture bag of claim 17, wherein the wash outlet is connected to a wash inlet located in the lower portion of the culture bag.

19. The culture bag of claim 17, wherein the lower portion comprises from about 1% to about 5% of the internal volume.

20. An acoustophoretic system, comprising:
the culture bag of claim 17;
at least one ultrasonic transducer including a piezoelectric material that is configured to be driven to create a multi-dimensional acoustic standing wave in the culture bag; and
means for moving the at least one ultrasonic transducer relative to the culture bag between the upper end and the lower end thereof.

21. The acoustophoretic system of claim 20, further comprising a tank into which the culture bag can be placed, and wherein the means for moving the at least one ultrasonic transducer is a conveyor system located outside of the tank.

22. The acoustophoretic system of claim 20, further comprising means for sealing the culture bag between the upper portion and the lower portion thereof.

23. An acoustophoretic system, comprising:
an acoustophoretic device comprising a feed port, a drain port located below the feed port and configured to operate as (i) a wash inlet and (ii) a concentrate outlet, a waste outlet, and at least one ultrasonic transducer including a piezoelectric material that is configured to be driven to create an acoustic standing wave; and
a selector valve connected to the feed port and to the drain port of the acoustophoretic device.

24. The acoustophoretic system of claim 23, further comprising the selector valve coupled to a feed input or a wash input.

25. The acoustophoretic system of claim 24, further comprising a feed selector valve coupled to the feed input and the wash input and the selector valve.

26. The acoustophoretic system of claim 25, further comprising the feed selector valve being upstream of the selector valve.

27. The acoustophoretic system of claim 25, further comprising an outflow selector valve connected to the drain port and the waste outlet.

* * * * *